United States Patent [19]

Tsipursky et al.

[11] Patent Number: 5,721,306
[45] Date of Patent: Feb. 24, 1998

[54] VISCOUS CARRIER COMPOSITIONS, INCLUDING GELS, FORMED WITH AN ORGANIC LIQUID CARRIER AND A LAYERED MATERIAL:POLYMER COMPLEX

[75] Inventors: Semeon Tsipursky, Lincolnwood; Gary W. Beall, McHenry; Anatoliy Sorokin, Buffalo Grove; Anatoliy Goldman, Palatine, all of Ill.

[73] Assignee: AMCOL International Corporation, Arlington Heights, Ill.

[21] Appl. No.: 525,416

[22] Filed: Sep. 8, 1995

Related U.S. Application Data

[63] Continuation-in-part of Ser. No. 488,264, Jun. 7, 1995, Pat. No. 5,552,467, and a continuation-in-part of Ser. No. 480,080, Jun. 7, 1995, Pat. No. 5,578,672, and a continuation-in-part of Ser. No. 488,263, Jun. 7, 1995.

[51] Int. Cl.⁶ .................. C08K 3/34; C08K 5/10; C08K 5/06; C08K 5/05
[52] U.S. Cl. .................. 524/449; 523/203; 523/207; 523/209; 523/212; 523/216; 524/312; 524/376; 524/377; 524/445; 524/446; 524/447; 524/451; 524/548; 524/557; 524/702; 524/789; 524/791; 524/379; 524/386; 501/4
[58] Field of Search .................. 524/449, 445, 524/446, 447, 789, 791, 376, 377, 312, 702, 451, 548, 557, 379, 386; 523/203, 212, 207, 209, 216; 501/4

[56] References Cited

U.S. PATENT DOCUMENTS

| | | | |
|---|---|---|---|
| 3,419,460 | 12/1968 | Ure | 161/162 |
| 3,419,517 | 12/1968 | Hedrick et al. | 260/37 |
| 3,515,626 | 6/1970 | Duffield | 161/162 |
| 3,773,708 | 11/1973 | Takahashi et al. | 260/41 R |
| 3,795,650 | 3/1974 | Burns | 260/33.4 R |
| 3,912,532 | 10/1975 | Simone | 106/308 N |
| 3,929,678 | 12/1975 | Laughlin et al. | 252/526 |
| 4,125,411 | 11/1978 | Lyons | 106/291 |
| 4,210,572 | 7/1980 | Herman et al. | 260/404 |
| 4,251,576 | 2/1981 | Osborn et al. | 428/331 |
| 4,400,485 | 8/1983 | Mukamal et al. | 524/444 |
| 4,431,755 | 2/1984 | Weber et al. | 523/203 |
| 4,434,075 | 2/1984 | Mardis et al. | 252/315.2 |
| 4,472,538 | 9/1984 | Kamigaito et al. | 523/202 |
| 4,500,670 | 2/1985 | McKinley et al. | 524/445 |
| 4,546,145 | 10/1985 | Kishida et al. | 524/780 |
| 4,600,744 | 7/1986 | Libor et al. | 524/446 |
| 4,613,542 | 9/1986 | Alexander | 428/290 |
| 4,624,982 | 11/1986 | Alexander | 524/446 |
| 4,739,007 | 4/1988 | Okada et al. | 524/789 |
| 4,789,403 | 12/1988 | Rice | 106/417 |
| 4,798,766 | 1/1989 | Rice | 428/404 |
| 4,810,734 | 3/1989 | Kawasumi et al. | 523/216 |
| 4,842,651 | 6/1989 | Ravet et al. | 106/487 |
| 4,889,885 | 12/1989 | Usuki et al. | 524/443 |
| 4,894,411 | 1/1990 | Okada et al. | 524/710 |
| 4,920,171 | 4/1990 | Hutton, Jr. et al. | 524/446 |
| 5,032,546 | 7/1991 | Giannelis et al. | 501/3 |
| 5,032,547 | 7/1991 | Giannelis et al. | 501/3 |
| 5,091,462 | 2/1992 | Fukui et al. | 524/504 |
| 5,102,948 | 4/1992 | Deguchi et al. | 524/789 |
| 5,164,440 | 11/1992 | Deguchi et al. | 524/444 |
| 5,164,460 | 11/1992 | Yano et al. | 624/445 |
| 5,204,078 | 4/1993 | Tateyama et al. | 423/331 |
| 5,206,284 | 4/1993 | Fukui et al. | 524/504 |
| 5,229,451 | 7/1993 | Carter et al. | 524/493 |
| 5,248,720 | 9/1993 | Deguchi et al. | 524/444 |
| 5,326,500 | 7/1994 | Friedman et al. | 252/378 |
| 5,340,558 | 8/1994 | Friedman et al. | 423/328.1 |
| 5,385,776 | 1/1995 | Maxfield et al. | 428/297 |
| 5,391,437 | 2/1995 | Miyasaka et al. | 524/446 |
| 5,414,042 | 5/1995 | Yasue et al. | 524/789 |
| 5,428,094 | 6/1995 | Tokoh et al. | 524/446 |
| 5,506,046 | 4/1996 | Andersen et al. | 524/446 |
| 5,508,072 | 4/1996 | Andersen et al. | 524/446 |

FOREIGN PATENT DOCUMENTS

| | | |
|---|---|---|
| 0 205 281 A3 | 12/1986 | European Pat. Off. |
| 0 335 653 A1 | 10/1989 | European Pat. Off. |
| 0 358 415 A1 | 3/1990 | European Pat. Off. |
| 0 479 031 A1 | 4/1992 | European Pat. Off. |
| 1146668 | 3/1969 | United Kingdom |
| WO 93/04117 | 3/1993 | WIPO |
| WO 93/04118 | 3/1993 | WIPO |

OTHER PUBLICATIONS

C. W. Francis, "Adsorption of Polyvinylpyrrolidone on Reference Clay Minerals", Soil Science, vol. 115, No. 1, 1973, pp. 40–54.

A. Usuki, et al., "Synthesis of nylon 6–clay hybrid", J. Mater. Res., vol. 8, No. 5, May 1993, pp. 1179–1184.

Y. Kojima, et al., "Mechanical Properties of Nylon 6–Clay Hybrid", J. Mater. Res., vol. 8, No. 5, May 1993, pp. 1185–1189.

K. Suzuki, et al., "Preparation of Delaminated Clay Having A Narrow Micropore Distribution In The Presence of Hydroxyaluminum Cations and Polyvinyl Alcohol", Clays and Clay Minerals, vol. 36, No. 2, 1988, pp. 147–152.

(List continued on next page.)

*Primary Examiner*—Peter A. Szekely
*Attorney, Agent, or Firm*—Marshall, O'Toole, Gerstein, Murray & Borun

[57] ABSTRACT

Intercalates formed by contacting the layer material, e.g., a phyllosilicate, with an intercalant polymer to sorb or intercalate the polymer between adjacent platelets of the layered material. Sufficient intercalant polymer is sorbed between adjacent platelets to expand the adjacent platelets to a spacing of at least about 50 Å (as measured after water removal to a maximum of 5% by weight water), up to about 100 Å and preferably in the range of about 10–45 Å, so that the intercalate easily can be exfoliated into individual platelets. The intercalated complex is combined with an organic liquid into an unexpectedly viscous carrier material, for delivery of the carrier material, or for delivery of an active compound, e.g., a pharmaceutical, or cosmetic, or lubricant, e.g., food guide lubricants dissolved or dispersed in the carrier material. Alternatively, the intercalated complex can be exfoliated prior to combination with the organic liquid.

90 Claims, 16 Drawing Sheets

OTHER PUBLICATIONS

R. Levy, et al., "Interlayer Adsorption of Polyvinylpyrrolidone On Montmorillonite", Journal of Colloid and Interface Science, vol. 50, No. 3, Mar. 1975, pp. 442–450.

D.J. Greeland, "Adsorption Of Polyvinyl Alcohols By Montmorillonite", Journal of Colloid Science, 18 (1963) pp. 647–664.

R.A. Vaia, et al., "Synthesis and Properties of Two–Dimensional Nanostructures by Direct Intercalation of Polymer Melts in Layered Silicates", Chem. Mater. 1993, 5, pp. 1694–1696.

R.A. Vaia, et al., "New Polymer Electrolyte nanocomposites: Melt intercalation of Poly(ethylene oxide) in Mica–Type Silicates", Advanced Materials 1995, 7, No. 2, pp. 154–156.

A. Akelah, et al., "Synthesis and Characterization of Epoxyphilic montmorillonites", Clay Minerals (1994) 29, pp. 169–178.

C.E. Clapp, et al., "Adsorption Studies Of A Dextran On Montmorillonite", Trans. 9th Int. Cong. Soil Sci., 1968, vol. 1, pp. 627–634.

H.G.G. Dekking, "Preparation And Properties Of Some Polymer–Clay Compounds", Clays and Clay Minerals, 1964, 12, pp. 603–616.

A. Usuki et al., "Characterization and Properties of Nylon 6—Clay Hybrid", (source and date unknown), pp. 651–652.

G.W. Brindley, et al., "Preparation And Solvatio Properties Of Some Variable Charge Montmorillonites", Clays and Clay Minerals, 1971, vol. 18, pp. 399–404.

A. Okada et al., "A Solid State NMR Study On Crystalline Forms Of Nylon 6", Journal of Applied Polymer Science, (1989), vol. 37, pp. 1363–1371.

A. Usuki et al., "Swelling Behavior Of Montmorillonite Cation Exchanged For ω–Amino Acids By ε–Caprolactam", J. Mater. Res., vol. 8, No. 5, May 1993, pp. 1174–1178.

Y. Kojima, et al., "One–Pot Synthesis Of Nylon 6–Clay Hybrid", Journal of Polymer Science: Part A: Polymer Chemistry, vol. 31, (1993), pp. 1755–1758.

Y. Kojima, et al., "Fine Structure Of Nylon–6–Clay Hybrid", Journal of Polymer Science: Part B: Polymer Physics, vol. 32 (1994), pp. 625–630.

B.K.G. Theng, "Clay–Polymer interactions: Sumary And Perspectives", Clays and Clay Minerals, vol. 30, No. 1 (1982) pp. 1–9.

Sugahara, et al., "Clay–Organic Nano–Composite; Preparation of a Kaolinite–Poly(vinylpyrrolidone) Intercalation Compound", Journal of the Ceramic Society of Japan, International Edition, vol. 100, No. 4, Apr. 1, 1992, pp. 420–423.

Ogawa et al., "Preparation Of Montmorillonite–Polyacrylamide Intercalation Compounds And The Water Absorbing Property", Clay Science, vol. 7, 1989 Tokyo, Japan, pp. 243–251.

Wu, et al., "Structural, thermal, and electrical characterization of layered nanocomposites derived from sodium–montmorillonite and polyethers", Chemical Abstracts, vol. 119, No. 4, Jul. 26, 1993 Columbus, Ohio, US, Abstract No. 31017r.

Bujdak, et al., "The reaction of montmorillonite with octadecylamine in solid and melted state", Chemical Abstracts, vol. 118, No. 26, Abstract No. 257609b, p. 166 (28 Jun. 1993), Columbus, Ohio (US).

Yano, et al., "Synthesis And Properties Of Polyimide–Clay Hybrid", Polymer Preprints, ACS, Apr. 1991, pp. 65–66.

Giannelis, et al., "Synthesis And Processing Of Ceramics: Scientific Issues", Materials Research Society Symposium Proceedings, vol. 249 (1992), pp. 547–558.

Search Report for WO 93/04118 which was submitted with Applicants' Information Disclosure Statement filed Dec. 5, 1995, identified as B3.

VISCOUS CARRIER COMPOSITIONS, INCLUDING GELS, FORMED WITH AN ORGANIC LIQUID CARRIER AND A LAYERED MATERIAL:POLYMER COMPLEX

CROSS-REFERENCE TO RELATED APPLICATIONS

This application is a continuation-in-part of application Ser. Nos. 08/488,264; now U.S. Pat. Nos. 5,552,469 Ser. No. 08/480,080 now U.S. Pat. No. 5,578,672 and Ser. No. 08/488,263, pending all filed Jun. 7, 1998.

FIELD OF THE INVENTION

The present invention is directed to viscous carrier or viscous solvent compositions useful for carrying active organic compounds, such as glycols; glycerols; alcohols; ketones; and other organic liquids; pigments; drugs; skin moisturizers; hair care compounds, e.g., silicone oils and silicone fluids; permanent waving lotion and hair relaxer reducing agents, and other hair care compounds, such as moisturizers, shampoos, hair conditioners, and shampoos/conditioners; oven cleaners; car wash compositions; cosmetics; alcohols and other de-icers for airplane wings and the like; lotions, ointments and creams; drug carriers for various pharmaceuticals and drugs, particularly for topical administration of medications, such as topical wound and burn medicaments. The viscous carrier compositions are formed from intercalated layered materials, and/or exfoliates thereof, manufactured by sorption of one or more intercalant compounds, e.g., oligomers or polymers between planar layers of a swellable layered material, such as a phyllosilicate or other layered material, to expand the interlayer spacing of adjacent layers to at least about 5 Å, preferably at least about 10 Å. The intercalates and/or exfoliates are combined with an organic liquid carrier to viscosify the carrier. The intercalates and exfoliates are described in our above-identified co-pending parent applications. The intercalated layered materials preferably have at least two layers of oligomer and/or polymer molecules sorbed on the internal surfaces between adjacent layers of the planar platelets of the layered material, such as a phyllosilicate, preferably a smectite clay, to expand the interlayer spacing to at least about 5 Angstroms, preferably at least about 10 Angstroms, more preferably to at least about 20 Angstroms, and most preferably to at least about 30–45 Angstroms, up to about 100 Å, or disappearance of periodicity. The resulting intercalates are neither entirely organophilic nor entirely hydrophilic, but a combination of the two, and easily can be exfoliated for or during admixture with a carrier or solvent to provide a stable, thixotropic composition, preferably a stable gel, capable of carrying any liquid hydrophilic or hydrophobic compound, particularly organic liquid compounds, and combinations of hydrophilic and hydrophobic liquids.

BACKGROUND OF THE INVENTION AND PRIOR ART

It is well known that phyllosilicates, such as smectite clays, e.g., sodium montmorillonite and calcium montmorillonite, can be treated with organic molecules, such as organic ammonium ions, to intercalate the organic molecules between adjacent, planar silicate layers, thereby substantially increasing the interlayer (interlaminar) spacing between the adjacent silicate layers. The thus-treated, intercalated phyllosilicates, then can be exfoliated, e.g., the silicate layers are separated, e.g., mechanically, by high shear mixing. The individual silicate layers, when admixed with a matrix polymer, before, after or during the polymerization of the matrix polymer, e.g., a polyamide—see U.S. Pat. Nos. 4,739,007; 4,810,734; and 5,385,776—have been found to substantially improve one or more properties of the polymer, such as mechanical strength and/or high temperature characteristics.

Exemplary of such prior art composites, also called "nanocomposites", are disclosed in published PCT disclosure of Allied Signal, Inc. WO 93/04118 and U.S. Pat. No. 5,385,776, disclosing the admixture of individual platelet particles derived from intercalated layered silicate materials, with a polymer to form a polymer matrix having one or more properties of the matrix polymer improved by the addition of the exfoliated intercalate. As disclosed in WO 93/04118, the intercalate is formed (the interlayer spacing between adjacent silicate platelets is increased) by adsorption of a silane coupling agent or an onium cation, such as a quaternary ammonium compound, having a reactive group which is compatible with the matrix polymer. Such quaternary ammonium cations are well known to convert a highly hydrophilic clay, such as sodium or calcium montmorillonite, into an organophilic clay capable of sorbing organic molecules. A publication that discloses direct intercalation (without solvent) of polystyrene and poly (ethylene oxide) in organically modified silicates is *Synthesis and Properties of Two-Dimensional Nanostructures by Direct Intercalation of Polymer Melts in Layered Silicates*, Richard A. Vaia, et al., *Chem. Mater.*, 5:1694–1696(1993). Also as disclosed in *Adv. Materials*, 7, No. 2: (1985), pp, 154–156, *New Polymer Electrolyte Nanocomposites: Melt Intercalation of Poly(Ethylene Oxide) in Mica-Type Silicates*, Richard A. Vaia, et al., poly(ethylene oxide) can be intercalated directly into Na-montmorillonite and Li-montmorillonite by heating to 80° C. for 2–6 hours to achieve a d-spacing of 17.7 Å. The intercalation is accompanied by displacing water molecules, disposed between the clay platelets with polymer molecules. Apparently, however, the intercalated material could not be exfoliated and was tested in pellet form. It was quite surprising to one of the authors of these articles that exfoliated material could be manufactured in accordance with the present invention.

Previous attempts have been made to intercalate polyvinylpyrrolidone (PVP), polyvinyl alcohol (PVOH) and poly (ethylene oxide) (PEO) between montmorillonite clay platelets with little success. As described in Levy, et al., *Interlayer Adsorption of Polyvinylpyrrolidone on Montmorillonite*, Journal of Colloid and Interface Science, Vol. 50, No. 3, March 1975, pages 442–450, attempts were made to sorb PVP (40,000 average M.W.) between monoionic montmorillonite clay platelets (Na, K, Ca and Mg) by successive washes with absolute ethanol, and then attempting to sorb the PVP by contact with 1% PVP/ethanol/water solutions, with varying amounts of water, via replacing the ethanol solvent molecules that were sorbed in washing (to expand the platelets to about 17.7 Å). Only the sodium montmorillonite had expanded beyond a 20 Å basal spacing (e.g., 26 Å and 32 Å), at $5^+$% $H_2O$, after contact with the PVP/ethanol/$H_2O$ solution. It was concluded that the ethanol was needed to initially increase the basal spacing for later sorption of PVP, and that water did not directly affect the sorption of PVP between the clay platelets (Table II, page 445), except for sodium montmorillonite. The sorption was time consuming and difficult and met with little success.

Further, as described in Greenland, *Adsorption of Polyvinyl Alcohols by Montmorillonite*, Journal of Colloid Sciences, Vol. 18, pages 647–664 (1963), polyvinyl alcohols containing 12% residual acetyl groups could increase the basal spacing by only about 10 Å due to the sorbed polyvinyl alcohol (PVOH). As the concentration of polymer in the intercalant polymer-containing solution was increased from 0.25% to 4%, the amount of polymer sorbed was substantially reduced, indicating that sorption might only be effective at polymer concentrations in the intercalant polymer-containing composition on the order of 1% by weight polymer, or less. Such a dilute process for intercalation of polymer into layered materials would be exceptionally costly in drying the intercalated layered materials for separation of intercalate from the polymer carrier, e.g., water, and, therefore, apparently no further work was accomplished toward commercialization.

In accordance with one embodiment of the present invention, intercalates are prepared by contacting a phyllosilicate with a PVP polymer, preferably essentially alcohol-free, or a PVOH intercalant polymer composition, wherein the PVOH preferably contains 5% or less residual acetyl groups, more preferably fully hydrolyzed, containing 1% or less acetyl groups.

In accordance with an important feature of the present invention, best results are achieved using a water soluble oligomer (herein defined as a prepolymer having 2 to about 15 recurring monomeric units, which can be the same or different) or polymer (herein defined as having more than about 15 recurring monomeric units, which can be the same or different) composition for intercalation having at least about 2%, preferably at least about 5% by weight, more preferably at least about 10% by weight intercalant oligomer or intercalant polymer concentration, most preferably about 30% to about 80% by weight oligomer and/or polymer, based on the weight of oligomer and/or polymer and carrier (e.g., water with or without another solvent for the intercalant oligomer or intercalant polymer) to achieve better sorption of the intercalant polymers between phyllosilicate platelets. Regardless of the concentration of polymer in liquid solvent of the intercalating composition, the intercalating composition should have a polymer:layered material ratio of at least 1:20, preferably at least 1:10, more preferably at least 1:5, and most preferably about 1:4 to achieve efficient intercalation of the polymer between adjacent platelets of the layered material. The oligomer or polymer sorbed between and permanently bonded to the silicate platelets causes separation or added spacing between adjacent silicate platelets and, for simplicity of description, both the oligomers and polymers are hereinafter called the "intercalant" or "intercalant polymer" or "polymer intercalant". In this manner, the oligomers or polymers will be sorbed sufficiently to increase the interlayer spacing of the phyllosilicate in the range of about 5 Å to about 100 Å, preferably at least about 10 Å, for easier and more complete exfoliation, in a commercially viable process, regardless of the particular phyllosilicate or intercalant polymer.

A phyllosilicate, such as a smectite clay, can be intercalated sufficiently for subsequent exfoliation by sorption of polymers or oligomers that have carbonyl, hydroxyl, carboxyl, amine, amide, ether, ester, sulfate, sulfonate, sulfinate, sulfamate, phosphate, phosphonate, phosphinate functionalities, or aromatic rings to provide metal cation chelate-type bonding between two functional groups of one or two intercalant polymer molecules and the metal cations bonded to the inner surfaces of the phyllosilicate platelets. Sorption and metal cation electrostatic attraction or bonding of a platelet metal cation between two oxygen or nitrogen atoms of the molecules; or the electrostatic bonding between the interlayer cations in hexagonal or pseudohexagonal rings of the smectite layers and an intercalant polymer aromatic ring structure increases the interlayer spacing between adjacent silicate platelets or other layered material to at least about about 5 Å, preferably at least about 10 Å, and more preferably at least about 20 Å, and most preferably in the range of about 30 Å to about 45 Å. Such intercalated phyllosilicates easily can be exfoliated into individual phyllosilicate platelets before or during admixture with a liquid carrier or solvent, for example, one or more monohydric alcohols, such as methanol, ethanol, propanol, and/or butanol; polyhydric alcohols, such as glycerols and glycols, e.g., ethylene glycol, propylene glycol, butylene glycol, glycerine and mixtures thereof; aldehydes, ketones, carboxylic acids; amines; amides; and other solvents, for delivery of the solvent in a thixotropic composition, or for delivery of any active hydrophobic or hydrophilic organic compound, such as a typically active pharmaceutical, dissolved or dispersed in the carrier or solvent, in a thixotropic composition.

Depending upon the conditions that the composition is subjected to during intercalation and exfoliation, particularly temperature; pH; and amount of water contained in the intercalating composition, the intercalate and/or exfoliate/carrier composition can be formed to any desired viscosity, e.g., at least about 100 centipoises, preferably at least about 500–1000 centipoises, whether or not gelled, and particularly to extremely high viscosities of about 5,000 to about 5,000,000 centipoises. The compositions are thixotropic so that shearing will lower viscosity for easier delivery, and then by reducing shear or eliminating shear, the compositions will increase in viscosity. The intercalant polymer intercalates between the spaces of adjacent platelets of the layered material for easy exfoliation, and complexes with the metal cations on the platelet surfaces where the polymer remains after the intercalant, or exfoliate thereof, is combined with the carrier/solvent. It is theorized that the polymer coating on the surfaces of the clay platelets is ionically complexed with interlayer cations and participates (aids) in the viscosification and thixotropy of the carrier/solvent composition. However, other forms of bonding such as hydrogen bonding or Van Der Waals forces or molecular complexing also may be responsible for the adherence of the polymer to the surfaces of the layered material, either entirely, or in part.

DEFINITIONS

Whenever used in this Specification, the terms set forth shall have the following meanings:

"Layered Material" shall mean an inorganic material, such as a smectite clay mineral, that is in the form of a plurality of adjacent, bound layers and has a thickness, for each layer, of about 3 Å to about 50 Å, preferably about 10 Å.

"Platelets" shall mean individual layers of the Layered Material.

"Intercalate" or "Intercalated" shall mean a Layered Material that includes oligomer and/or polymer molecules disposed between adjacent platelets of the Layered Material to increase the interlayer spacing between the adjacent platelets to at least about 5 Å, preferably at least about 10 Å.

"Intercalation" shall mean a process for forming an Intercalate.

"Intercalant Polymer" or "Intercalant" shall mean an oligomer or polymer that is sorbed between Platelets of the Layered Material and complexes with the platelet surfaces to form an Intercalate.

"Intercalating Carrier" shall mean a carrier comprising water with or without an organic solvent used together with an Intercalant Polymer to form an Intercalating Composition capable of achieving Intercalation of the Layered Material.

"Intercalating Composition" shall mean a composition comprising an Intercalant Polymer, an Intercalating Carrier for the Intercalant Polymer, and a Layered Material.

"Exfoliate" or "Exfoliated" shall mean individual platelets of an Intercalated Layered Material so that adjacent platelets of the Intercalated Layered Material can be dispersed individually throughout a carrier material, such as water, an alcohol or glycol, or any other organic solvent.

"Exfoliation" shall mean a process for forming an Exfoliate from an Intercalate.

SUMMARY OF THE INVENTION

In brief, the present invention is directed to viscous, thixotropic carrier compositions comprising a liquid carrier or solvent composition containing intercalated and/or exfoliated platelets of a layered material. The intercalated layered material is formed by contacting a layered material, such as a phyllosilicate, with an oligomer and/or polymer to sorb or intercalate the intercalant polymer or mixtures of intercalant polymers between adjacent phyllosilicate platelets. Sufficient intercalant polymer is sorbed between adjacent phyllosilicate platelets to expand the spacing between adjacent platelets (interlayer spacing) to a distance of at least about 5 Å, preferably at least about 10 Å (as measured after water removal to a maximum water content of 5% by weight) and preferably in the range of about 30–45 Å, so that the intercalate easily can be exfoliated, sometimes naturally, without shearing being necessary. At times, the intercalate requires shearing for exfoliation that easily can be accomplished, e.g., when mixing the intercalate with the carrier or solvent, to provide a composition of carrier or solvent and exfoliated platelets of the layered material having a desired viscosity of about 20 centipoises to about 5,000,000 centiposes, preferably at least about 500 centipoises.

The viscous compositions can be in the form of a stable thixotropic gel that is not subject to phase separation and can be used to deliver any active materials, such as in the cosmetic, hair care and pharmaceutical industries. The layered material is intercalated and optionally exfoliated by contact with an intercalant polymer and water and then mixed and/or extruded to intercalate the polymer between adjacent phyllosilicate platelets and optionally separate (exfoliate) the layered material into individual platelets. The amount of water varies, depending upon the amount of shear imparted to the layered material in contact with the polymer and water. In one method, the intercalating composition is pug milled or extruded. At a water content of about 25% by weight to about 50% by weight water, preferably about 35% to about 40% by weight water, based on the dry weight of the layered material, e.g., clay. In another method, the clay and water are slurried, with at least about 25% by weight water, based on the dry weight of the layered material, e.g., preferably less than about 20% by weight clay in water, based on the total weight of layered material and water, more preferably less than about 10% layered material in water, with the addition of about 2% by weight to about 90% by weight polymer, based on the dry weight of the layered material.

In accordance with a preferred embodiment of the present invention, the intercalant polymer should be water-soluble (herein defined as sufficiently soluble such that at least 0.1 gram of the polymer will dissolve per 100 grams of distilled water at 25° C.). In accordance with a preferred embodiment of the present invention, the intercalant polymer should include an aromatic ring and/or have a functionality selected from the group consisting of a carbonyl; carboxyl; hydroxyl; amine; amide; ether; ester, sulfate, solfonate, sulfinate, sulfamate, phosphate, phosphonate, phosphinate functionality, or an aromatic ring to be sufficiently complexed or bound to the platelet surfaces of the layered material. It is hereby theorized that polymer binding to the platelet surfaces is by metal cation electrostatic bonding or complexing, e.g., chelation, of the metal cations of the phyllosilicate sharing electrons with two carbonyl, two carboxyl, two hydroxyl, two oxygen, two amine, two $SO_x$, two $PO_x$ (wherein x=2, 3, or 4) and/or two amide functionalities of one intercalant polymer molecule, or of two adjacent intercalant polymer molecules to an inner surface of the phyllosilicate platelets. Such intercalant polymers have sufficient affinity for the phyllosilicate platelets to provide sufficient interlayer spacing for exfoliation, e.g., about 5 Å–100 Å, preferably about 10 Å–50 Å, and to maintain attachment to the surfaces of the platelets, without the need for coupling agents or spacing agents, such as the onium ion or silane coupling agents disclosed in the above-mentioned prior art.

Sorption of the intercalant polymer should be sufficient to achieve expansion of adjacent platelets of the layered material (when measured dry—having a maximum of about 5% by weight water) to an interlayer spacing of at least about 5 Å, preferably a spacing of at least about 10 Å, more preferably a spacing of at least about 20 Å, and most preferably a spacing of about 30–45 Å. To achieve intercalates that can be exfoliated easily using the preferred water-soluble polymer intercalants disclosed herein, such as polyvinylpyrrolidone, polyvinyl alcohol, and mixtures thereof, the weight ratio of intercalant polymer to layered material, preferably a water-swellable smectite clay such as sodium bentonite, in the intercalating composition contacting the phyllosilicate should be at least about 1:20, preferably at least about 1:12 to 1:10, more preferably at least about 1:5, and most preferably about 1:5 to about 1:3. It is preferred that the concentration of polymer in the intercalating composition, based on the total weight of polymer plus intercalant carrier (water plus any organic liquid solvent) in the intercalating composition is at least about 15% by weight, more preferably at least about 20% by weight polymer, for example about 20%–30% to about 90% by weight polymer, based on the weight of polymer plus intercalant carrier (water plus any organic solvent) in the intercalant composition during intercalation.

It has been found that the intercalates of the present invention are increased in interlayer spacing step-wise. If the phyllosilicate is contacted with an intercalating composition containing less than about 16% by weight intercalant polymer, e.g., 10% to about 15% by weight polymer, based on the dry weight of the phyllosilicate, a monolayer width of intercalant polymer is sorbed (intercalated) between the adjacent platelets of the layered material. A monolayer of polymer intercalated between platelets increases the interlayer spacing to about 5 Å to less than about 10 Å. When the amount of intercalant polymer is in the range of about 16% to less than about 35% by weight, based on the weight of the dry layered material, the intercalant polymer is sorbed in a bilayer, and each layer complexes separately with one of two adjacent platelet surfaces, thereby increasing the interlayer spacing to about 10 Å to about 16 Å, as shown in FIGS. 1 and 2. At an intercalant polymer loading in the intercalating composition of about 35% to less than about 55% intercalant polymer, based on the dry weight of the layered material in the intercalating composition, the interlayer spacing is increased to about 20 Å to about 25 Å, corresponding to three layers of intercalant polymer sorbed between adjacent platelets of the layered material, as shown in FIGS. 1 and 2. At an intercalant polymer loading of about 55% to about 80% intercalant polymer, based on the dry weight of the layered material in the intercalating composition, the interlayer spacing will be increased to about 30 Å to about 35 Å, corresponding to 4 and 5 layers of intercalant polymer sorbed (intercalated) between and complexed to adjacent platelets of the layered material, as shown in FIGS. 1 and 2.

Such interlayer spacings have never been achieved by direct intercalation of an oligomer or polymer molecule, without prior sorption of a coupling agent, such as an onium or silane coupling agent, and provides easier and more complete exfoliation for or during incorporation of the platelets into a carrier or solvent to provide unexpectedly viscous carrier compositions, for delivery of the carrier, or for administration of an active compound that is dissolved or dispersed in the carrier or solvent. Such compositions, especially the high viscosity gels, are particularly useful for delivery of active compounds, such as oxidizing agents for hair waving lotions, and drugs for topical administration, since extremely high viscosities are obtainable; and for admixtures of the platelets with polar solvents in modifying rheology, e.g., of cosmetics, oil-well drilling fluids, paints, lubricants, especially food grade lubricants in the manufacture of oil and grease, and the like.

Once exfoliated, the platelets of the intercalate are predominantly completely separated into individual platelets having intercalant polymer molecules complexed with the platelet surfaces, and the originally adjacent platelets no longer are retained in a parallel, spaced disposition, but are free to move as predominantly individual, polymer coated (continuously or discontinuously) platelets throughout a carrier or solvent material to maintain viscosity and thixotropy of the carrier material. The predominantly individual phyllosilicate platelets, having their platelet surfaces complexed with polymer molecules, are randomly, homogeneously and uniformly dispersed, predominantly as individual platelets, throughout the carrier or solvent to achieve new and unexpected viscosities in the carrier/platelet compositions even after addition of an active organic compound, such as a cosmetic component or a medicament, for administration of the active organic compound(s) from the composition.

As recognized, the thickness of exfoliated, individual clay platelets (about 10 Å) is relatively small compared to the size of the flat opposite polymer-complexed platelet faces. The clay platelets have an aspect ratio in the range of about 200 to about 2,000. Dispersing such finely divided platelet particles into an organic liquid carrier or solvent provides a very large area of contact between carrier and platelet particles, for a given volume of particles in the composition, and provides a high degree of platelet homogeneity and unexpectedly high viscosity to the composition.

The polymer intercalants used to form the intercalates and/or exfoliates used in the compositions of the present invention need not have any (but can include) reactivity with the carrier or solvent in which the inventive intercalates and/or exfoliates are dispersed, while improving one or more properties, particularly viscosity, of the carrier or solvent material.

Figure 14:
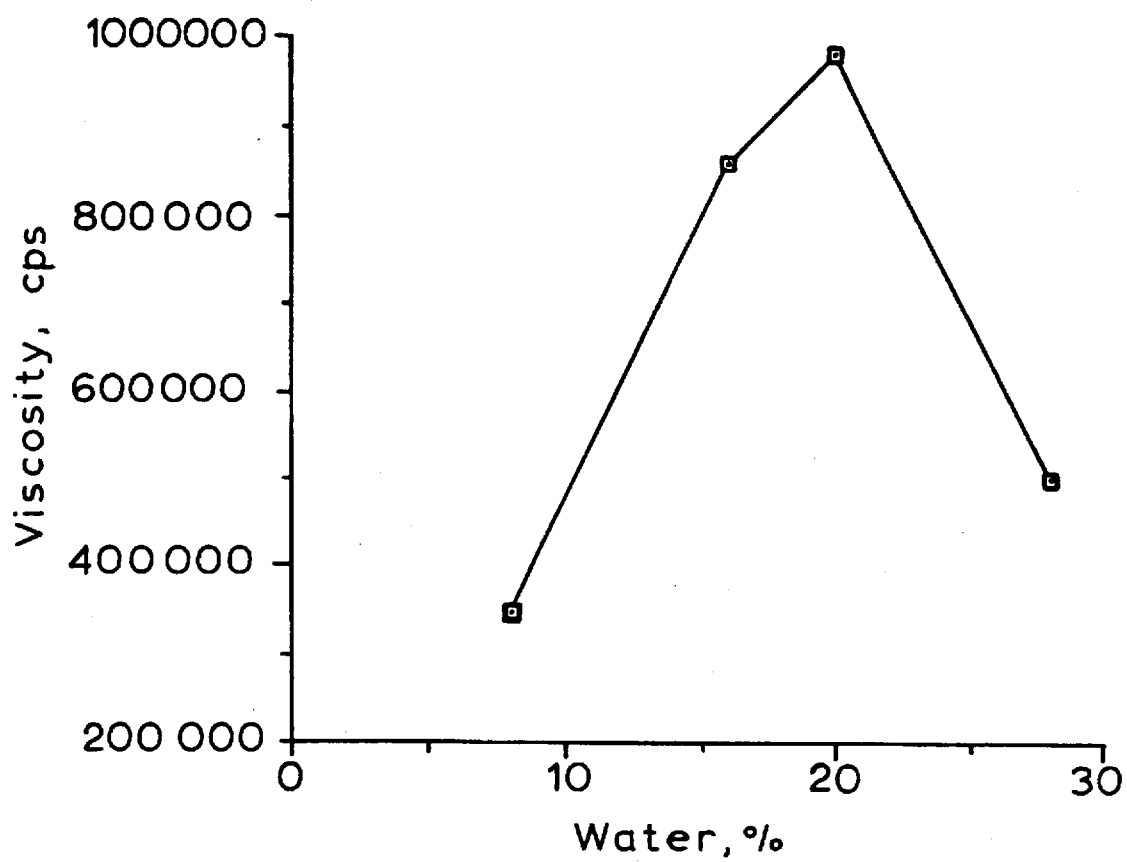
Figure 15:
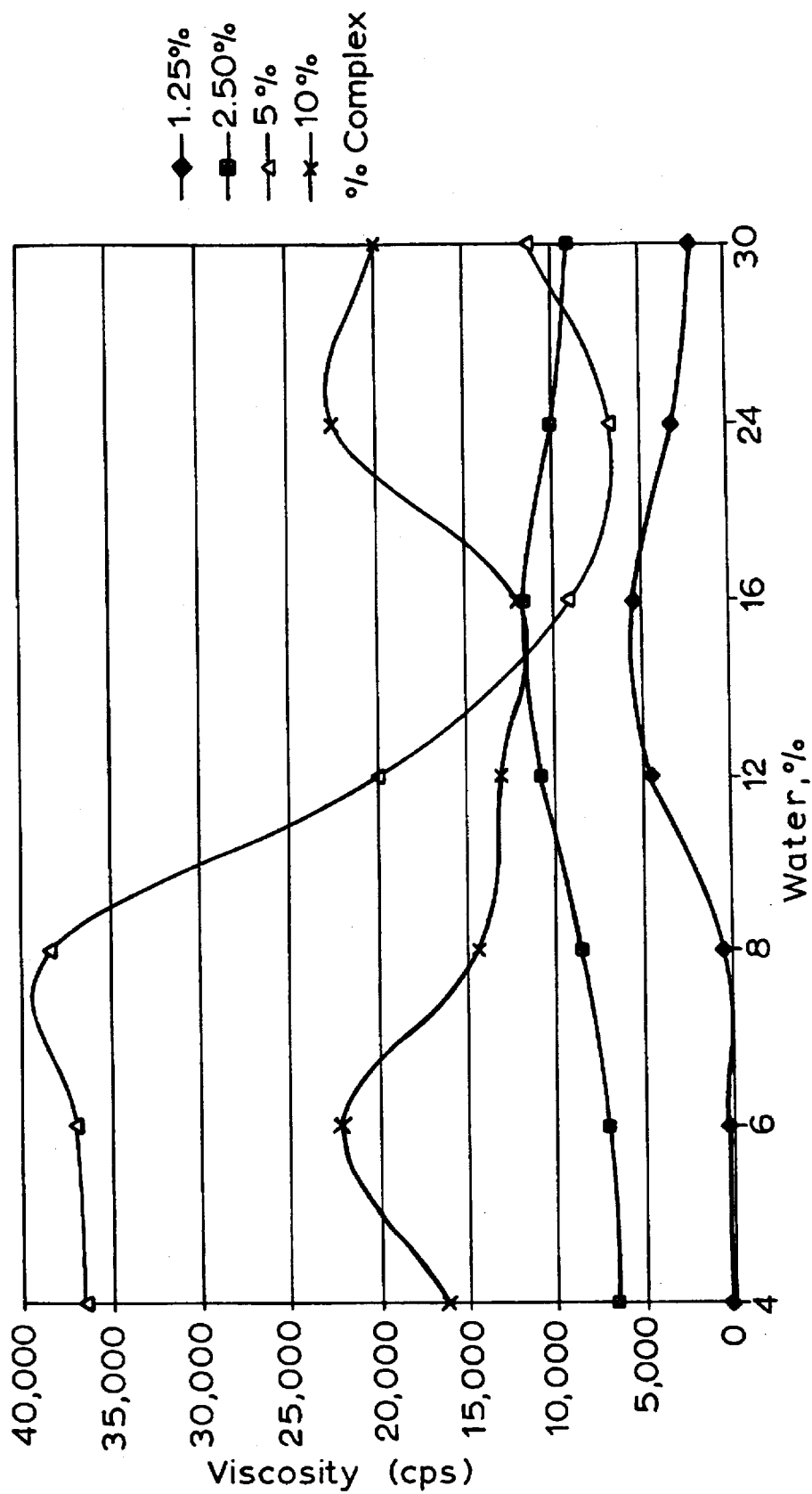
Figure 16:
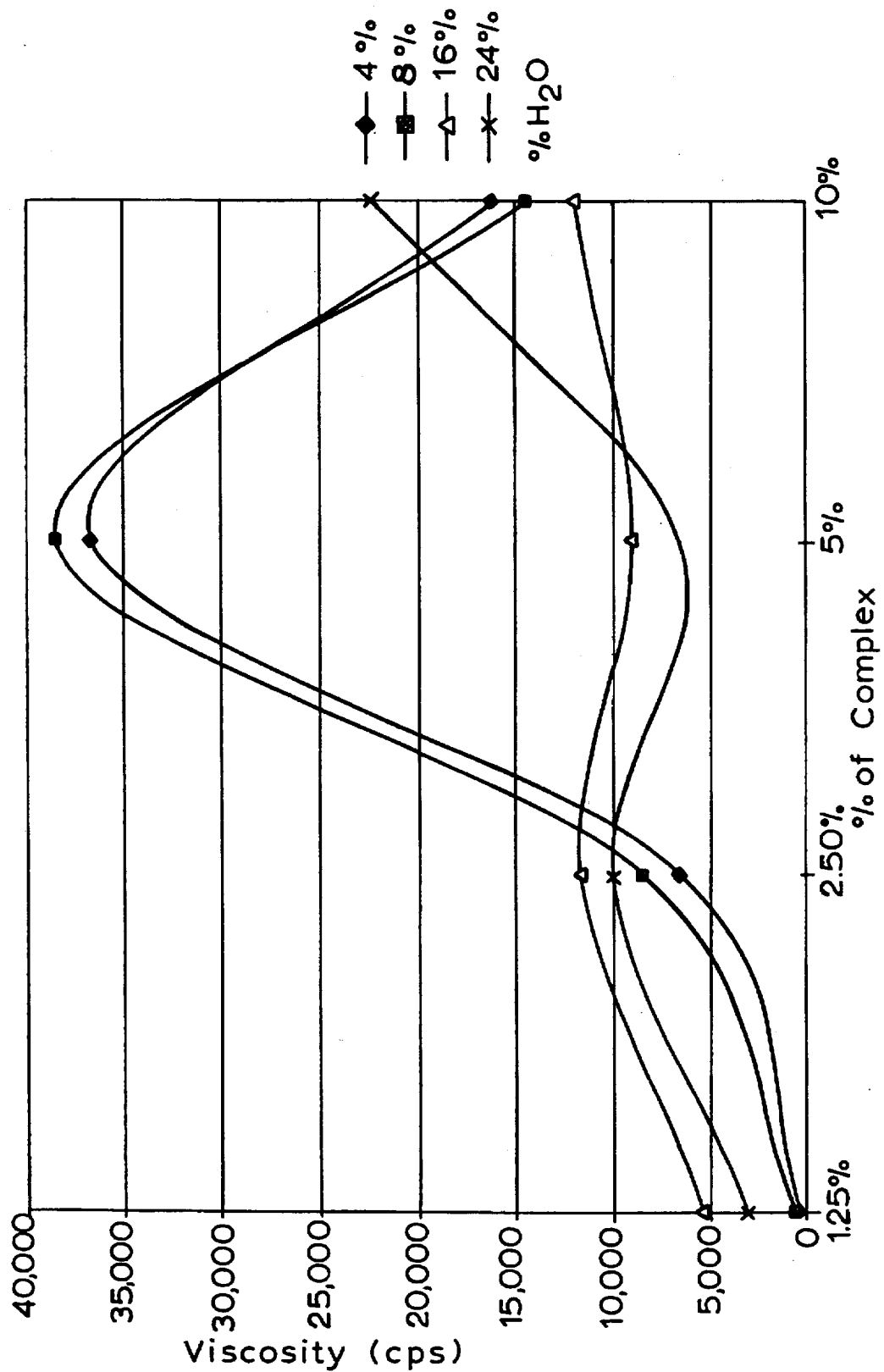
Figure 17:
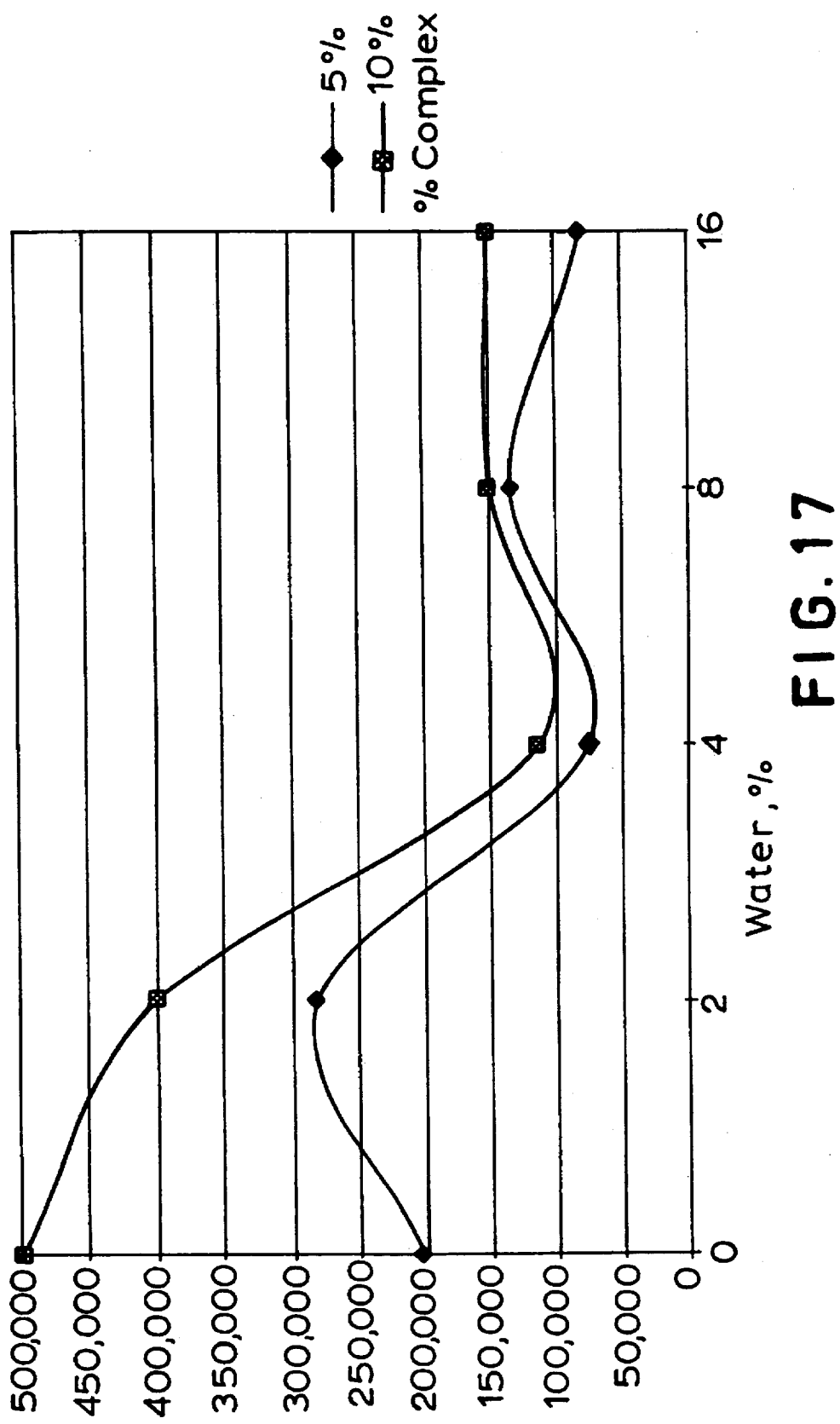

FIG. 14 is a graph of composition viscosity at 24° C. of compositions containing 10% by weight Na bentonite:PVP complex (4:1 weight ratio) mixed with water at about 8% to about 28% water and about 72% by weight to about 92% by weight ethanol (water plus ethanol=100%) showing an increase in viscosity with added water between about 8% water and about 20% water by weight and a decrease in viscosity with more than about 20% by weight water;

FIGS. 15 and 16 are graphs of composition viscosity at 24° C. of compositions of varied percentages of water and propylene glycol at various loadings between about 1.25% by weight and about 10% by weight of a complex of Na bentonite clay:PVP (4:1 clay:PVP weight ratio) showing the change in viscosity at various $H_2O$ percentages ($H_2O$ plus propylene glycol=100%) and at various clay:PVP complex loadings; and FIG. 17 is a graph of composition viscosity at 24° C. of compositions of varied percentages of water and glycerol at 0–16% by weight water and 84–100% by weight glycerol at 5% by weight and 10% by weight loadings of a complex of Na bentonite clay:PVP (4:1 clay:PVP weight ratio) showing the change in viscosity at various water percentages ($H_2O$ plus glycerol=100%) at various clay:PVP complex loadings.

DETAILED DESCRIPTION OF THE PREFERRED EMBODIMENTS

To form the intercalated materials useful in admixture with the carriers or solvents in accordance with the present invention, the phyllosilicate should be swelled or intercalated by sorption of an oligomer or polymer that includes an aromatic ring and/or a functionality selected from the group consisting of carbonyl; carboxyl; hydroxyl; amine; amide; ether; ester, sulfate, sulfonate, sulfinate, sulfamate, phosphate, phosphonate, phosphinate, or combinations thereof. In accordance with a preferred embodiment of the present invention, the intercalating composition should include at least about 4% by weight water, up to about 5000% by weight water, based on the dry weight of the phyllosilicate, preferably about 7% to about 100% water, more preferably about 25% to about 50% by weight water, prior to or during contact with the intercalant polymer to achieve sufficient intercalation for exfoliation. Preferably, the phyllosilicate should include at least about 4% by weight water before contact with the intercalating carrier for efficient intercalation. The amount of intercalant polymer in contact with the phyllosilicate from the intercalating composition, for efficient exfoliation, should provide an intercalant polymer/phyllosilicate weight ratio (based on the dry weight of the phyllosilicate) of at least about 1:20, preferably at least about 3.2:20, and more preferably about 4–14:20, to provide efficient sorption and complexing (intercalation) of the polymer between the platelets of the layered material, e.g., phyllosilicate, (preferably about 16 to about 70 percent by weight intercalant polymer, based on the dry weight of the layered silicate material).

The preferred polymer intercalants are water-soluble and are added to the intercalating composition in the form of a solid or liquid (neat or aqueous solution or dispersion, with or without a liquid organic solvent, e.g., alcohol) having an intercalant polymer concentration of at least about 2%, preferably at least about 5% by weight polymer, more preferably at least about 50% to about 100% by weight intercalant polymer in the intercalating composition, based on the dry weight of the layered material, for intercalant polymer sorption. The polymer can be added as a solid with the addition to the layered material/polymer blend of at least about 20% water, preferably at least about 30% water to about 5000% water or more, based on the dry weight of the layered material, with or without another solvent for the intercalant polymer. Preferably about 30% to about 50% water, more preferably about 30% to about 40% by weight water, based on the dry weight of the layered material, is included in the intercalating composition, when extruding or pug milling, so that less water or solvent is sorbed by the intercalate, thereby necessitating less drying energy after intercalation. The intercalant polymer may be introduced into the spaces between every layer, nearly every layer, or at least a predominance of the layers of the layered material such that the subsequently exfoliated platelet particles are preferably, predominantly less than about 5 layers in thickness; more preferably, predominantly about 1 or 2 layers in thickness; and most preferably, predominantly single platelets.

Any swellable layered material that sufficiently sorbs the intercalant polymer to increase the interlayer spacing between adjacent phyllosilicate platelets to at least about 5 Å, preferably at least about 10 Å (when the phyllosilicate spacing is measured dry—having a maximum of about 5% by weight water) may be used in the practice of this invention. Useful swellable layered materials include phyllosilicates, such as smectite clay minerals, e.g., montmorillonite, particularly sodium montmorillonite; magnesium montmorillonite and/or calcium montmorillonite; nontronite; beidellite; volkonskoite; hectorite; saponite; sauconite; sobockite; stevensite; svinfordite; vermiculite; and the like. Other useful layered materials include micaceous minerals, such as illite and mixed layered illite/smectite minerals, such as rectorite, tarosovite, ledikite and admixtures of illites with the clay minerals named above.

Other layered materials having little or no charge on the layers may be useful in this invention provided they can be intercalated with the intercalant polymers to expand their interlayer spacing to at least about 5 Å, preferably to at least about 10 Å. Preferred swellable layered materials are phyllosilicates of the 2:1 type having a negative charge on the layers ranging from about 0.15 to about 0.9 charges per formula unit and a commensurate number of exchangeable metal cations in the interlayer spaces. Most preferred layered materials are smectite clay minerals such as montmorillonite, nontronite, beidellite, volkonskoite, hectorite, saponite, sauconite, sobockite, stevensite, and svinfordite.

As used herein the "interlayer spacing" refers to the distance between the internal faces of the adjacent dry layers as they are assembled in the layered material before any delamination (exfoliation) takes place. The interlayer spacing is measured when the layered material is "air dry", e.g., contains about 3–10% water, preferably about 3–6% by weight water, based on the dry weight of the layered material. The preferred clay materials generally include interlayer cations such as $Na^+$, $Ca^{+2}$, $K^+$, $Mg^{+2}$, $NH_4^+$ and the like, including mixtures thereof.

The amount of intercalant polymer intercalated into the swellable layered materials useful in this invention, in order that the intercalated layered material platelet surfaces sufficiently complex with the polymer molecules, such that the layered material may be easily exfoliated or delaminated into individual platelets, may vary substantially between about 10% and about 80%, based on the dry weight of the layered silicate material. In the preferred embodiments of the invention, amounts of polymer intercalants employed, with respect to the dry weight of layered material being intercalated, will preferably range from about 8 grams of intercalant polymer/100 grams of layered material (dry basis), preferably at least about 10 grams of polymer/100 grams of layered material to about 80–90 grams intercalant polymer/100 grams of layered material. More preferred amounts are from about 20 grams intercalant polymer/100 grams of layered material to about 60 grams intercalant polymer/100 grams of layered material (dry basis).

The polymer intercalants are introduced into (sorbed within) the interlayer spaces of the layered material in one of two ways. In a preferred method of intercalating, the layered material is intimately mixed, e.g., by extrusion or pug milling, to form an intercalating composition comprising the layered material, in an intercalant polymer or intercalant polymer/water solution, or intercalant polymer, water and an organic solvent. To achieve sufficient intercalation for exfoliation, the layered material/intercalant polymer blend contains at least about 8% by weight, preferably at least about 10% by weight intercalant polymer, based on the dry weight of the layered material. The intercalating carrier (preferably water, with or without an organic solvent) can be added by first solubilizing or dispersing the intercalant polymer in the carrier; or the dry intercalant polymer and relatively dry phyllosilicate (preferably containing at least about 4% by weight water) can be blended and the intercalating carrier added to the blend, or to the phyllosilicate prior to adding the dry intercalant polymer. In every case, it has been found that surprising sorption and complexing of intercalant polymer between platelets is achieved at relatively low loadings of intercalating carrier, especially $H_2O$, e.g., at least about 4% by weight water, based on the dry weight of the phyllosilicate. When intercalating the phyllosilicate in slurry form (e.g. 900 pounds water, 100 pounds phyllosillicate, 25 pounds polymer) the amount of water can vary from a preferred minimum of at least about 30% by weight water, with no upper limit to the amount of water in intercalating composition (the phyllosilicate intercalate is easily separated from the intercalating composition).

Alternatively, the intercalating carrier, e.g., water, with or without an organic solvent, can be added directly to the phyllosilicate prior to adding the intercalant polymer, either dry or in solution. Sorption of the polymer intercalant molecules may be performed by exposing the layered material to dry or liquid polymer intercalant compositions containing at least about 2% by weight, preferably at least about 5% by weight intercalant polymer, more preferably at least about 50% intercalant polymer, based on the dry weight of the layered material. Sorption may be aided by exposure of the intercalating composition to heat, pressure, ultrasonic cavitation, or microwaves.

In accordance with another method of intercalating the intercalant polymer between the platelets of the layered material and exfoliating the intercalate, the layered material, containing at least about 4% by weight water, preferably about 10% to about 15% by weight water, is blended with an aqueous solution of a water-soluble intercalant polymer in a ratio sufficient to provide at least about 8% by weight, preferably at least about 10% by weight intercalant polymer, based on the dry weight of the layered material. The blend then preferably is extruded for faster intercation of the polymer with the layered material.

The preferred polymer intercalants are water-soluble, such as polyvinylpyrrolidone (PVP) having a monomeric structure (I) as follows:

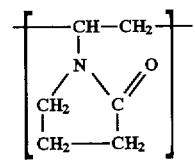

The water-solubility of PVP can be adjusted according to (1) the degree of hydrolysis of the polyvinylpyrrolidone, and (2) by forming a metal salt of PVP, such as sodium or potassium. PVP can be hydrolyzed to the structure (II):

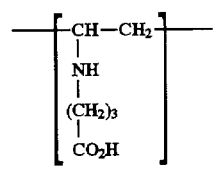

and the PVP, or copolymers of vinylpyrrolidone and a vinyl amide of γ-amine butyric acid, can be intercalated in the salt form, e.g., sodium or potassium polyvinylpyrrolidone polymers. Preferred PVP intercalants, and the following PVP derivatives, should have a weight average molecular weight in the range of about 100 to about 100,000 or more, more preferably about 1,000 to about 40,000.

Other suitable water-soluble vinyl polymers include poly (vinyl alcohol)

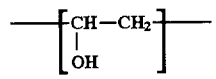

The polyvinyl alcohols function best when they are essentially fully hydrolyzed, e.g., 5% or less acetyl groups, preferably 1% or less residual acetyl groups. The lower molecular weight PVA's function best, e.g., a weight average molecular weight of about 2,000 to about 10,000, but higher molecular weights also function, e.g., up to about 100,000.

The polyacrylic acid polymers and copolymers and partially or fully neutralized salts, e.g., metal salts, are also suitable, having monomer units:

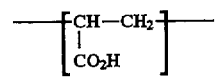

and are commercially available as CARBOPOL resins from B. F. Goodrich and PRIMAL resins from Rohm & Haas. Light cross-linking is acceptable, so long as water-solubility is retained. Weight average molecular weights, for the polyacrylic polymers and copolymers described above and below, of about 10,000 or less, e.g., 200–10,000, intercalate more easily, but higher molecular weights up to about 100,000 or more also function.

Other water-soluble derivatives of, and substituted, polyacrylic acids also are useful as intercalant polymers in accordance with the present invention, such as poly (methacrylic acid), (PMAA), having a monomeric structure:

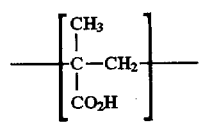

Similar water-soluble polymers and copolymers that are suitable in accordance with the present invention include poly(methacrylamide), or PMAAm, having a general monomeric structure:

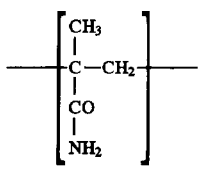

Poly(N,N-Dimethylacrylamide) having the general monomeric structure:

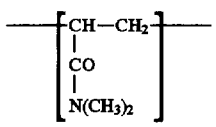

Poly(N-Isopropylacrylamide), or PIPAAm, having the monomeric structure:

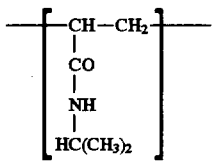

Poly(N-acetamidoacrylamide), having a monomeric structure:

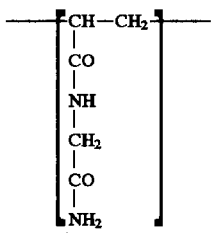

and Poly(N-acetmidomethacrylamide), having a monomeric structure:

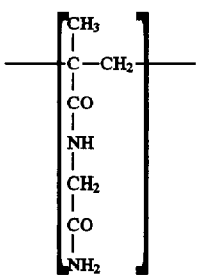

Water-soluble copolymers including any one or more of the above-described acrylic polymers also are useful in accordance with the principles of the present invention, including the acrylic interpolymers of polyacrylic acid and poly(methacrylic acid); polyacrylic acid with poly(methacrylamide); and polyacrylic acid with methacrylic acid.

Other suitable water-soluble polymers include polyvinyloxazolidone (PVO) and polyvinylmethyloxazolidone (PVMO), having the monomeric structures:

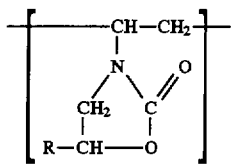

PVO:R = H
PVMO:R = $CH_3$

Also suitable are polyoxypropylene, polyoxyethylene block polymers that conform to the formulas:

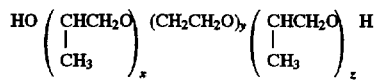

and

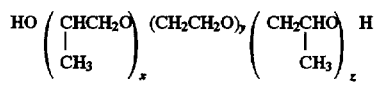

wherein x and z are each an integer in the range of about 4 to about 30; and y is an integer in the range of about 4 to about 100, for example Meroxapol 105; Meroxapol 108; Meroxapol 171; Meroxapol 172; Meroxapol 174; Meroxapol 178; Meroxapol 251; Meroxapol 252; Meroxapol 254; Meroxapol 255; Meroxapol 258; Meroxapol 311; Meroxapol 312; and Meroxapol 314.

Other suitable water-soluble/water-dispersible intercalant polymers include polyacrylamide and copolymers of acrylamide; acrylamide/sodium acrylate copolymer; acrylate/acrylamide copolymer; acrylate/ammonium methacrylate copolymer; acrylate/diacetoneacrylamide copolymers; acrylic/acrylate copolymers; adipic acid/dimethylaminohydroxypropyl diethylenetriamine copolymer; ammonium acrylate copolymers; ammonium styrene/acrylate copolymers; ammonium vinyl acetate/acrylate copolymers; aminomethanepropanol (AMP) acrylate/diacetoneacrylamide copolymers; aminomethylpropanediol (AMPD) acrylate/diacetoneacrylamide copolymers; butyl benzoic acid/phthalic anhydride/trimethylolethane copolymer; cornstarch/acrylamide/sodium acrylate copolymer; diethylene glycolamine/epichlorohydrin/piperazine copolymer; dodecanedioic acid/cetearyl alcohol/glycol copolymers; ethylene/vinyl alcohol copolymer; ethyl ester of polyethyleneimines, such as hydroxyethyl/PEI-1000 and hydroxyethyl PEI-1500; isopropyl ester of, polyvinyl methacrylate/methacrylic acid (PVM/MA) copolymer; melamine/formaldehyde resin; methacryloyl ethyl betaine/methacrylate copolymers; methoxy PEG-22/dodecyl glycol copolymer; octadecene/maleic anhydride copolymer; octylacrylamide/acrylate/butylaminoethyl methacrylate copolymers; octylacrylamide/acrylate copolymers; polyethylene glycol (PEG)/dodecyl glycol copolymers; polyvinylimines, such as, PEI-7; PEI-15; PEI-30; PEI-45; PEI-275; PEI-700; PEI-1000; PEI-1500; and PEI-2500; phthalic anhydride/glycerin/glycidyl decanoate copolymer; metal salts of acrylic and polyacrylic acid; polyaminopropyl biguanide; polymeric quaternary ammonium salts, such as polyquaternium-1; polyquaternium-2; polyquaternium-4; polyquaternium-5; polyquaternium-6; polyquaternium-7; polyquaternium-8; polyquaternium-9; polyquaternium-10; polyquaternium-11; polyquaternium-12; polyquaternium-13; polyquaternium-14; and polyquaternium-15; polyvinyl imidazolinium acetate; potassium polyacrylate; sodium polyacrylate; metal salts of PVM/MA copolymers, e.g. Li, K, Na, Ru, Ce salts; polyvinylpyrrolidone (PVP)/eicosene copolymers; PVP/ethyl methacrylate/methacrylic acid copolymer; PVP/hexadecene copolymer; polyvinylpyrrolidone/vinyl acetate (PVP/VA) copolymer; PVP/vinyl acetate/itaconic acid copolymer; sodium acrylate/vinyl alcohol copolymers; sodium $C_4$–$C_{12}$, and other metal salts of olefin/maleic acid copolymers; sodium polymethacrylate; sodium polystyrene sulfonate; sodium styrene/acrylate/PEG-10 dimaleate copolymer; water-soluble esters and ethers of cellulose; sodium styrene/PEG-10 maleate/nonoxynol-10 maleate/acrylate copolymer; starch/acrylate/acrylamide copolymers; styrene/acrylamide copolymer; styrene/acrylate/ammonium methacrylate copolymer; styrene/maleic anhydride copolymer; styrene/PVO copolymer; sucrose benzoate/sucrose acetate isobutyrate/butyl benzyl phthalate copolymer; sucrose benzoate/sucrose acetate isobutyrate/butyl benzylphthalate/ methyl methacrylate copolymer; urea/formaldehyde prepolymers; urea/melamine/formaldehyde prepolymers; vinyl acetate/crotonic acid copolymers; and vinyl alcohol copolymers.

Other water-soluble polymeric polyols and polyhydric alcohols, such as polysaccharides, also are suitable as polymer intercalants.

The amount of intercalated and/or exfoliated layered material included in the liquid carrier or solvent compositions to form the viscous compositions suitable to deliver the carrier or some carrier-dissolved or carrier-dispersed active material, such as a pharmaceutical, may vary widely depending on the intended use and desired viscosity of the composition. For example, relatively higher amounts of intercalates, i.e., from about 10% to about 30% by weight of the total composition, are used in forming solvent gels having extremely high viscosities, e.g., 5,000 to 5,000,000 centipoises. Extremely high viscosities, however, also can be achieved with a relatively small concentration of intercalates and/or exfoliates thereof, e.g., 0.1% to 5% by weight, by adjusting the pH of the composition in the range of about 0–6 or about 10–14 and/or by heating the composition above room temperature, e.g., in the range of about 25° C. to about 200° C., preferably about 75° C. to about 100° C. It is preferred that the intercalate or platelet loading be less than about 10% by weight of the composition. Intercalate or platelet particle loadings within the range of about 0.01% to about 40% by weight, preferably about 0.05% to about 20%, more preferably about 0.5% to about 10% of the total weight of the composition significantly increases the viscosity of the composition. In general, the amount of intercalate and/or platelet particles incorporated into the carrier/solvent is less than about 20% by weight of the total composition, and preferably from about 0.05% to about 20% by weight of the composition, more preferably from about 0.01% to about 10% by weight of the composition, and most preferably from about 0.01% to about 5%, based on the total weight of the composition.

In accordance with an important feature of the present invention, the intercalate and/or platelet/carrier compositions of the present invention can be manufactured in a concentrated form, e.g., as a master gel, e.g., having about 10–90%, preferably about 20–80% intercalate and/or exfoliated platelets of layered material and about 10–90%, preferably about 20–80% carrier/solvent. The master gel can be later diluted and mixed with additional carrier or solvent to reduce the viscosity of the composition to a desired level.

The intercalates, and/or exfoliates thereof, are mixed with a carrier or solvent to produce viscous compositions of the carrier or solvent optionally including one or more active compounds, such as an antiperspirant compound, dissolved or dispersed in the carrier or solvent.

In accordance with an important feature of the present invention, a wide variety of topically-active compounds can be incorporated into a stable composition of the present invention. Such topically active compositions include cosmetic, industrial, and medicinal compounds that act upon contact with the skin or hair, or are used to adjust rheology of industrial greases and the like. In accordance with another important feature of the present invention, a topically-active compound can be solubilized in the composition of the present invention or can be homogeneously dispersed throughout the composition as an insoluble, particulate material. In either case topically-effective compositions of the present invention are resistant to composition separation and effectively apply the topically-active compound to the skin or hair. If required for stability, a surfactant can be included in the composition, such as any disclosed in Laughlin, et al. U.S. Pat. No. 3,929,678, hereby incorporated by reference. In general, the topically-effective compositions of the present invention demonstrate essentially no phase separation if the topically-active compound is solubilized in the compositions. Furthermore, if the topically-active compound is insoluble in the composition, the composition demonstrates essentially no phase separation.

The topically-active compounds can be a cosmetically-active compound, a medically-active compound or any other compound that is useful upon application to the skin or hair. Such topically-active compounds include, for example, antiperspirants, antidandruff agents, antibacterial compounds, antifungal compounds, anti-inflammatory compounds, topical anesthetics, sunscreens and other cosmetic and medical topically-effective compounds.

Therefore, in accordance with an important feature of the present invention, the stable topically-effective composition can include any of the generally-known antiperspirant compounds such as finely-divided solid astringent salts, for example, aluminum chlorohydrate, aluminum chlorohydrox, zirconium chlorohydrate, and complexes of aluminum chlorohydrate with zirconyl chloride or zirconyl hydroxychloride. In general, the amount of the antiperspirant compound, such as aluminum zirconium tetrachlorohydrex glycine in the composition can range from about 0.01% to about 50%, and preferably from about 0.1% to about 30%, by weight of the total composition.

Other topically-active compounds can be included in the compositions of the present invention in an amount sufficient to perform their intended function. For example, zinc oxide, titanium dioxide or similar compounds can be included if the composition is intended to be a sunscreen. Similarly, topically-active drugs, like antifungal compounds; antibacterial compounds; anti-inflammatory compounds; topical anesthetics; skin rash, skin disease and dermatitis medications; and anti-itch and irritation-reducing compounds can be included in the compositions of the present invention. For example, analgesics such as benzocaine, dyclonine hydrochloride, aloe vera and the like; anesthetics such as butamben picrate, lidocaine hydrochloride, zylocaine and the like; antibacterials and antiseptics, such as povidone-iodine, polymyxin b sulfate-bactracin, zinc-neomycin sulfate-hydrocortisone, chloramphenicol, methylbenzethonium chloride, and erythromycin and the like; antiparasitics, such as lindane; deodorants, such as chlorophyllin copper complex, aluminum chloride, aluminum chloride hexahydrate, and methylbenzethonium chloride; essentially all dermatologicals, like acne preparations, such as benzoyl peroxide, erythromycin-benzoyl peroxide, clindamycin phosphate, 5,7-dichloro-8-hydroxyquinoline, and the like; anti-inflammatory agents, such as alclometasone dipropionate, betamethasone valerate, and the like; burn relief ointments, such as o-amino-p-toluenesulfonamide monoacetate and the like; depigmenting agents, such as monobenzone; dermatitis relief agents, such as the active steroids amcinonide, diflorasone diacetate, hydrocortisone, and the like; diaper rash relief agents, such as methylbenzethonium chloride and the like; emollients and moisturizers, such as mineral oil, PEG-4 dilaurate, lanolin oil, petrolatum, mineral wax and the like; fungicides, such as butocouazole nitrate, haloprogin, clotrimazole, and the like; herpes treatment drugs, such as 9-[(2-hydroxyethoxy)methyl]guanine; pruritic medications, such as alclometasone dipropionate, betamethasone valerate, isopropyl myristate MSD, and the like; psoriasis, seborrhea and scabicide agents, such as anthralin, methoxsalen, coal tar and the like; sunscreens, such as octyl p-(dimethylamino)benzoate, octyl methoxycinnamate, oxybenzone and the like; steroids, such as 2-(acetyloxy)-9-fluoro-1',2',3',4'-tetrahydro-11-hydroxypregna-1,4-dieno [16,17-b]naphthalene-3,20-dione, and 21-chloro-9-fluoro-1',2',3',4'-tetrahydro-11b-hydroxypregna-1,4-dieno[16z,17-b]naphthalene-3,20-dione. Any other medication capable of topical administration also can be incorporated in composition of the present invention in an amount sufficient to perform its intended function.

Eventual exfoliation of the intercalated layered material should provide delamination of at least about 90% by weight of the intercalated material to provide a more viscous composition comprising a carrier or solvent having polymer-complexed platelet particles substantially homogeneously dispersed therein. Some intercalates require a shear rate that is greater than about 10 sec$^{-1}$ for such relatively thorough exfoliation. Other intercalates exfoliate naturally or by heating, or by applying low pressure, e.g., 0.5 to 60 atmospheres above ambient, with or without heating. The upper limit for the shear rate is not critical. In the particularly preferred embodiments of the invention, when shear is employed for exfoliation, the shear rate is from greater than about 10 sec$^{-1}$ to about 20,000 sec$^{-1}$, and in the more preferred embodiments of the invention the shear rate is from about 100 sec$^{-1}$ to about 10,000 sec$^{-1}$.

When shear is employed for exfoliation, any method which can be used to apply a shear to the intercalant/carrier composition can be used. The shearing action can be provided by any appropriate method, as for example by mechanical means, by thermal shock, by pressure alteration, or by ultrasonics, all known in the art. In particularly useful procedures, the composition is sheared by mechanical methods in which the intercalate, with or without the carrier or solvent, is sheared by use of mechanical means, such as stirrers, Banbury® type mixers, Brabender® type mixers, long continuous mixers, and extruders. Another procedure employs thermal shock in which shearing is achieved by alternatively raising or lowering the temperature of the composition causing thermal expansions and resulting in internal stresses which cause the shear. In still other procedures, shear is achieved by sudden pressure changes in pressure alteration methods; by ultrasonic techniques in which cavitation or resonant vibrations which cause portions of the composition to vibrate or to be excited at different phases and thus subjected to shear. These methods of shearing are merely representative of useful methods, and any method known in the art for shearing intercalates may be used.

Mechanical shearing methods may be employed such as by extrusion, injection molding machines, Banbury® type mixers, Brabender® type mixers and the like. Shearing also can be achieved by introducing the layered material and intercalant polymer at one end of an extruder (single or double screw) and receiving the sheared material at the other end of the extruder. The temperature of the layered material/intercalant polymer composition, the length of the extruder, residence time of the composition in the extruder and the design of the extruder (single screw, twin screw, number of flights per unit length, channel depth, flight clearance, mixing zone, etc.) are several variables which control the amount of shear to be applied for exfoliation.

Exfoliation should be sufficiently thorough to provide at least about 80% by weight, preferably at least about 85% by weight, more preferably at least about 90% by weight, and most preferably at least about 95% by weight delamination of the layers to form individual platelet particles that can be substantially homogeneously dispersed in the carrier or solvent. As formed by this process, the platelet particles dispersed in the carrier or solvent have the thickness of the individual layers plus one to five monolayer thicknesses of complexed polymer, or small multiples less than about 10, preferably less than about 5 and more preferably less than about 3 of the layers, and still more preferably 1 or 2 layers. In the preferred embodiments of this invention, intercalation and delamination of every interlayer space is complete so that all or substantially all individual layers delaminate one from the other to form separate platelet particles for admixture with the carrier or solvent. The compositions can include the layered material as all intercalate, completely without exfoliation, initially to provide relatively low viscosities for transportation and pumping until it is desired to increase viscosity via easy exfoliation. In cases where intercalation is incomplete between some layers, those layers will not delaminate in the carrier or solvent, and will form platelet particles comprising those layers in a coplanar aggregate.

The effect of adding into a carrier or solvent the nanoscale particulate dispersed platelet particles, derived from the intercalates formed in accordance with the present invention, typically is a substantial increase in viscosity of the carrier or solvent.

The following specific clay:polymer complex preparations are presented to more particularly illustrate the invention and are not to be construed as limitations thereon.

Preparation of Clay—PVP Complexes (Intercalates)

Materials:

Clay—sodium montmorillonite;

PVP—molecular weights of 10,000 and 40,000.

To prepare Clay (sodium montmorillonite)—PVP complexes (intercalates) we used three different processes for polymer intercalation:

1. Mixture of the 2% PVP/water solution with the 2% clay/water suspension in a ratio sufficient to provide a polymer concentration of at least about 8% by weight, preferably at least about 10% by weight, based on the dry weight of the clay.

2. Dry clay powder (about 8% by weight moisture) was gradually added to the 2% PVP/water solution in a ratio sufficient to provide a polymer concentration of at least about 8% by weight, preferably at least about 10% by weight, based on the dry weight of the clay.

3. Dry PVP was mixed with dry clay, the mixture was hydrated with 25–50%, preferably 35%–40% by weight water, based on the dry weight of the clay, and then extruded.

Mixtures 1 and 2 were agitated at room temperature during 4 hours.

The weight ratio Clay:PVP was changed from 90:10 to 20:80.

Figure 1:
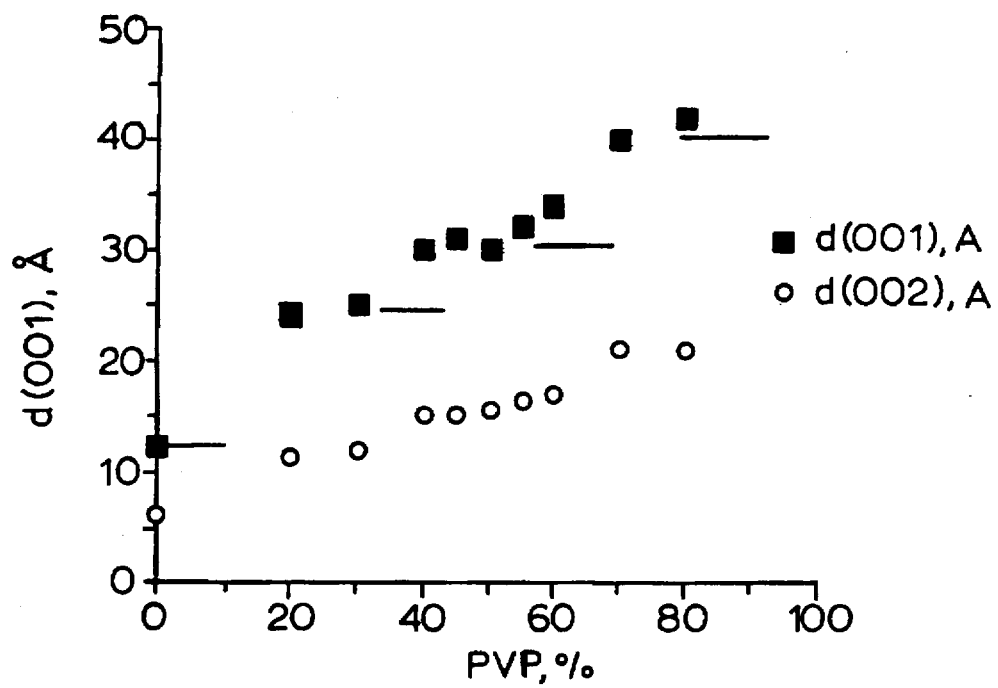
FIG. 1 is a graph plotting interlayer space for polyvinylpyrrolidone (PVP):smectite clay complexes (intercalates) showing d(001) and d(002) spacing, in Angstroms, between smectite clay platelets versus percentage of PVP sorbed, based on the dry weight of the smectite clay.

These experiments show that all methods of preparation yielded the Clay—PVP complexes (intercalates), and the results of the intercalation do not depend on the method of preparation (1, 2, or 3) or molecular weight of the intercalant polymer (PVP), but do depend on the ratio of clay:PVP in the intercalating composition. In Table 1 the results of the X-ray diffraction for Clay—PVP complexes with different ratios of components are demonstrated. The plot of these data is shown in FIG. 1. From these data (Table 1, FIG. 1) one can see the step character of intercalation while the polymer is being sorbed in the interlayer space between adjacent platelets of the montmorillonite clay. There are increasing d(001) values from 12 Å for clay with no PVP sorbed to 24–25 Å spacing between adjacent platelets with sorption of 20–30% PVP. The next step to 30–32 Å spacing occurs when the sorbed PVP content is increased to 40–60%. Further increasing the sorbed PVP content to 70–80% increases the d(001) values to 40–42 Å. There are d(002) reflexes together with d(001) reflexes in X-ray patterns of all complexes obtained (Table 1, FIG. 1). This indicates the regularity of Clay—PVP complex structures.

TABLE 1

|  | PVP, %* | d (001), Å | d (002), Å |
|---|---|---|---|
| 1 | 0.0 | 12.4 | 6.2 |
| 2 | 10.0 | 17.5 | 8.6 |
| 3 | 20.0 | 24.0 | 11.4 |
| 4 | 30.0 | 25.0 | 12.0 |
| 5 | 40.0 | 30.0 | 15.2 |
| 6 | 45.0 | 31.0 | 15.2 |
| 7 | 50.0 | 30.0 | 15.5 |
| 8 | 55.0 | 32.0 | 16.5 |
| 9 | 60.0 | 34.0 | 17.0 |
| 10 | 70.0 | 40.0 | 21.0 |
| 11 | 80.0 | 42.0 | 21.0 |

*Percent by weight, based on the dry weight of the clay plus polymer.

Preparation of Clay—PVA Complexes (Intercalates)

Materials:

Clay—sodium montmorillonite;

PVOH—degree of hydrolysis 75–99%, molecular weight of 10,000.

To prepare Clay (sodium montmorillonite)—PVOH complexes (intercalates) we provided three different processes for polymer intercalation:

1. Mixture of the 2% PVOH/water solution with the 2% clay/water suspension in a ratio sufficient to provide a polymer concentration of at least about 8% by weight, preferably at least about 10% by weight, based on the dry weight of the clay.

2. Dry clay powder was gradually added to the 2% PVOH/water solution in a ratio sufficient to provide a polymer concentration of at least about 8% by weight, preferably at least about 10% by weight, based on the weight of the clay.

3. Dry clay was moisturized with PVOH/water solution to a moisture content of 25%–80%, preferably about 35%–40% water, and then extruded.

The mixtures 1 and 2 were agitated at room temperature during 4 hours.

The weight ratio Clay:PVOH was changed from 80:20 to 20:80.

Figure 2:
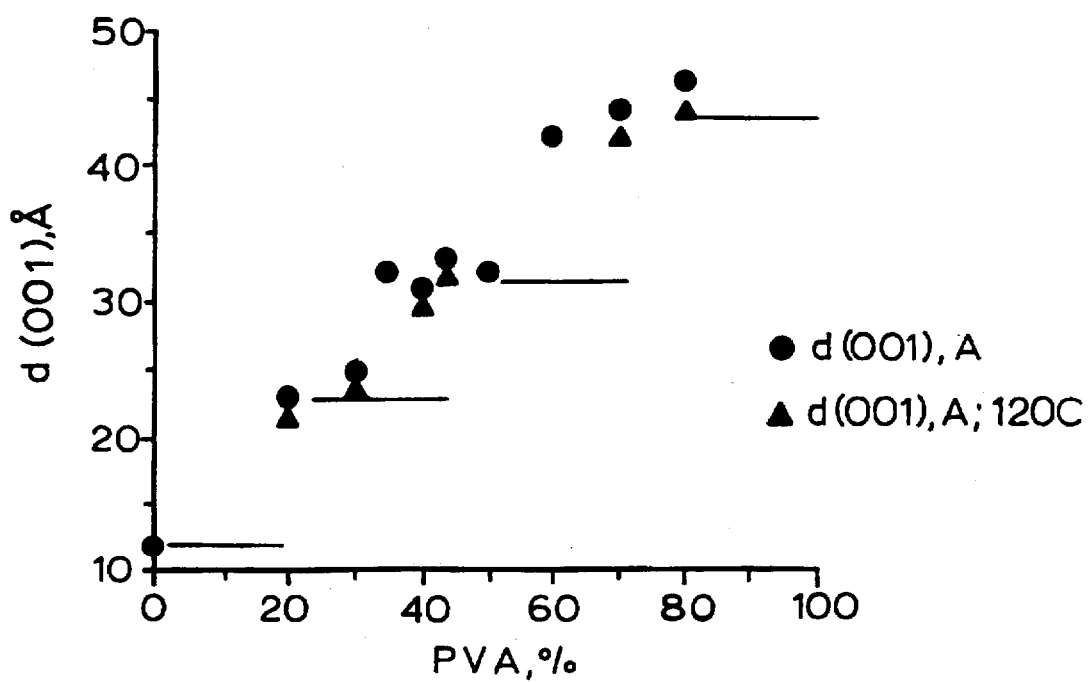
FIG. 2 is a graph plotting interlayer space for polyvinylalcohol (PVOH):smectite clay complexes (intercalates) showing d(001) spacing, in Angstroms, between smectite clay platelets versus percentage of PVOH sorbed, based on the dry weight of the smectite clay.

Some of the exfoliates were studied by X-ray diffraction. These experiments show that all methods of preparation yielded the composite Clay—PVOH complexes (intercalates), and the results of the intercalation do not depend on the method of preparation (1, 2, or 3), or molecular weight of the intercalant polymer (PVOH), or degree of hydrolysis, but do depend on the ratio of clay:PVOH in the intercalating composition. In Table 2 the results of the X-ray diffraction for Clay—PVOH complexes with different ratios of components are demonstrated. The plot of these data is shown in FIG. 2. From these data (Table 2, FIG. 2) one can see the step character of increasing d(001) values from 12 Å for clay with no sorbed PVOH to 22–25 Å spacing between adjacent platelets with sorption of 20–30% PVOH. The next step to 30–33 Å occurs when the sorbed PVOH content increases to 35–50%. A further increase of the sorbed PVOH content to 60–80% increases the d(001) values to 40–45 Å.

Heating of samples at 120° C. during 4 hours insignificantly changed the d(001) values (Table 2, FIG. 2).

TABLE 2

|  | PVOH %* | d (001), Å | d (001), Å 120° C. |
|---|---|---|---|
| 1 | 0.0 | 12.4 | 9.6 |
| 2 | 10.0 | 17.0 | 16.8 |
| 3 | 20.0 | 23.0 | 22.0 |
| 4 | 30.0 | 25.0 | 24.0 |
| 5 | 35.0 | 32.0 | 32.0 |
| 6 | 40.0 | 31.0 | 30.0 |
| 7 | 45.0 | 33.0 | 32.0 |
| 8 | 50.0 | 32.0 | 32.0 |
| 9 | 60.0 | 42.0 | 42.0 |
| 10 | 70.0 | 44.0 | 42.0 |
| 11 | 80.0 | 45.0 | 44.0 |

*Percent by weight, based on the dry weight of the clay plus PVOH.

Figure 3:
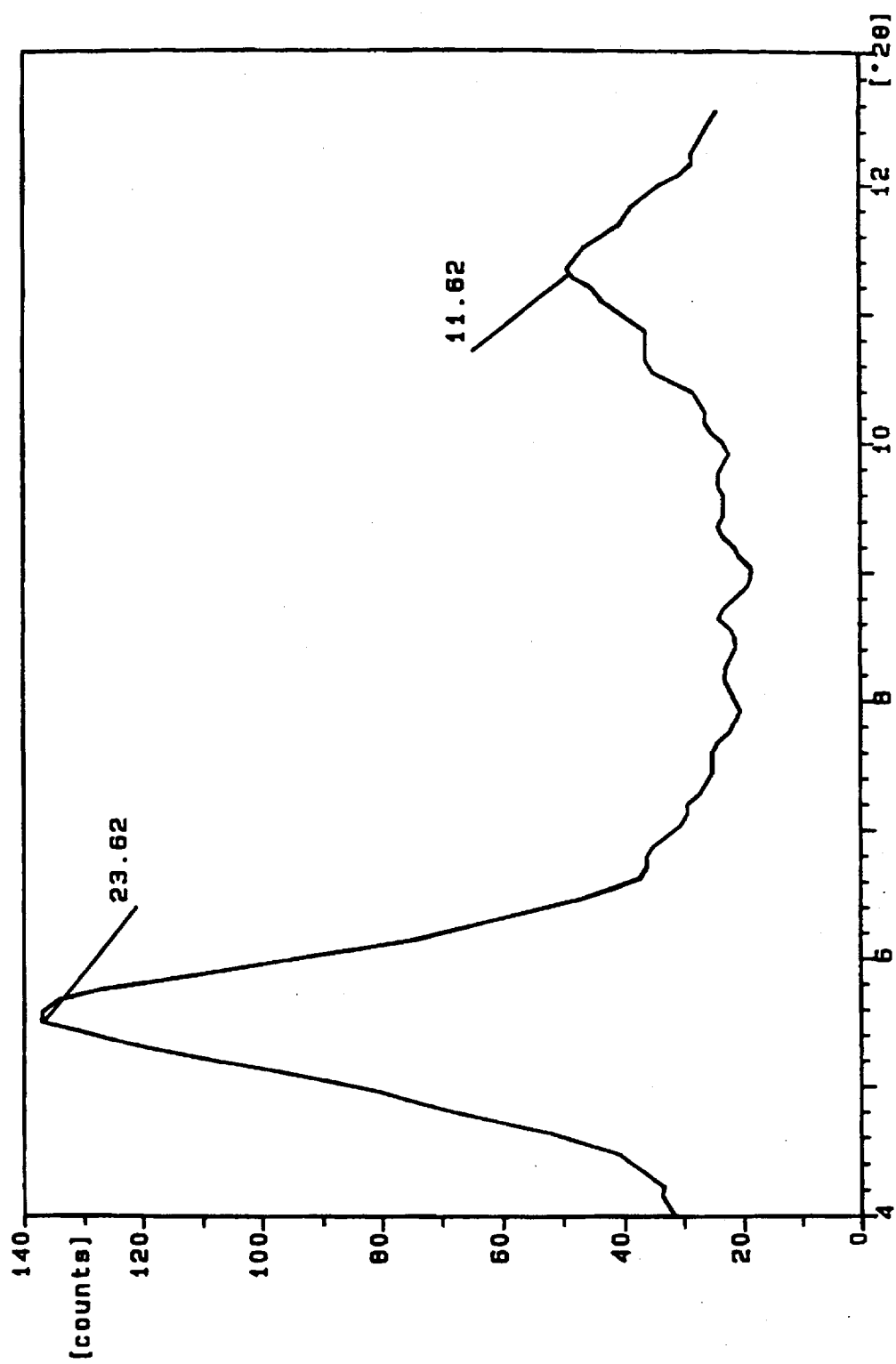
FIG. 3 is an x-ray diffraction pattern for a complex of PVP (weight average molecular weight of 10,000):sodium montmorillonite clay, in Angstroms, at a weight ratio of PVP:clay of 20:80.
Figure 4:
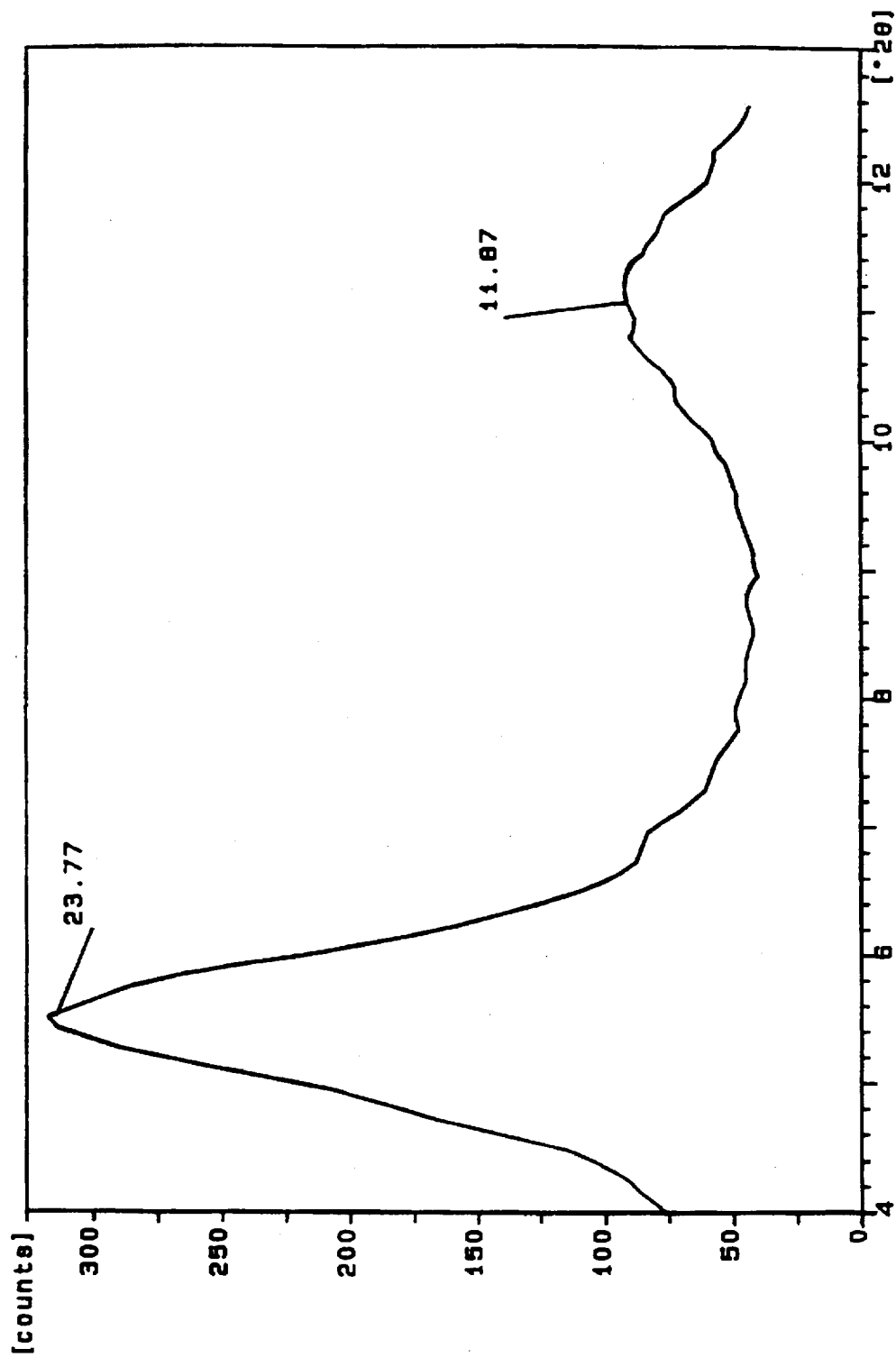
FIG. 4 is an x-ray diffraction pattern for a complex of PVP (weight average molecular weight of 40,000):sodium montmorillonite clay, in Angstroms, at a weight ratio of PVP:clay of 20:80.
Figure 5:
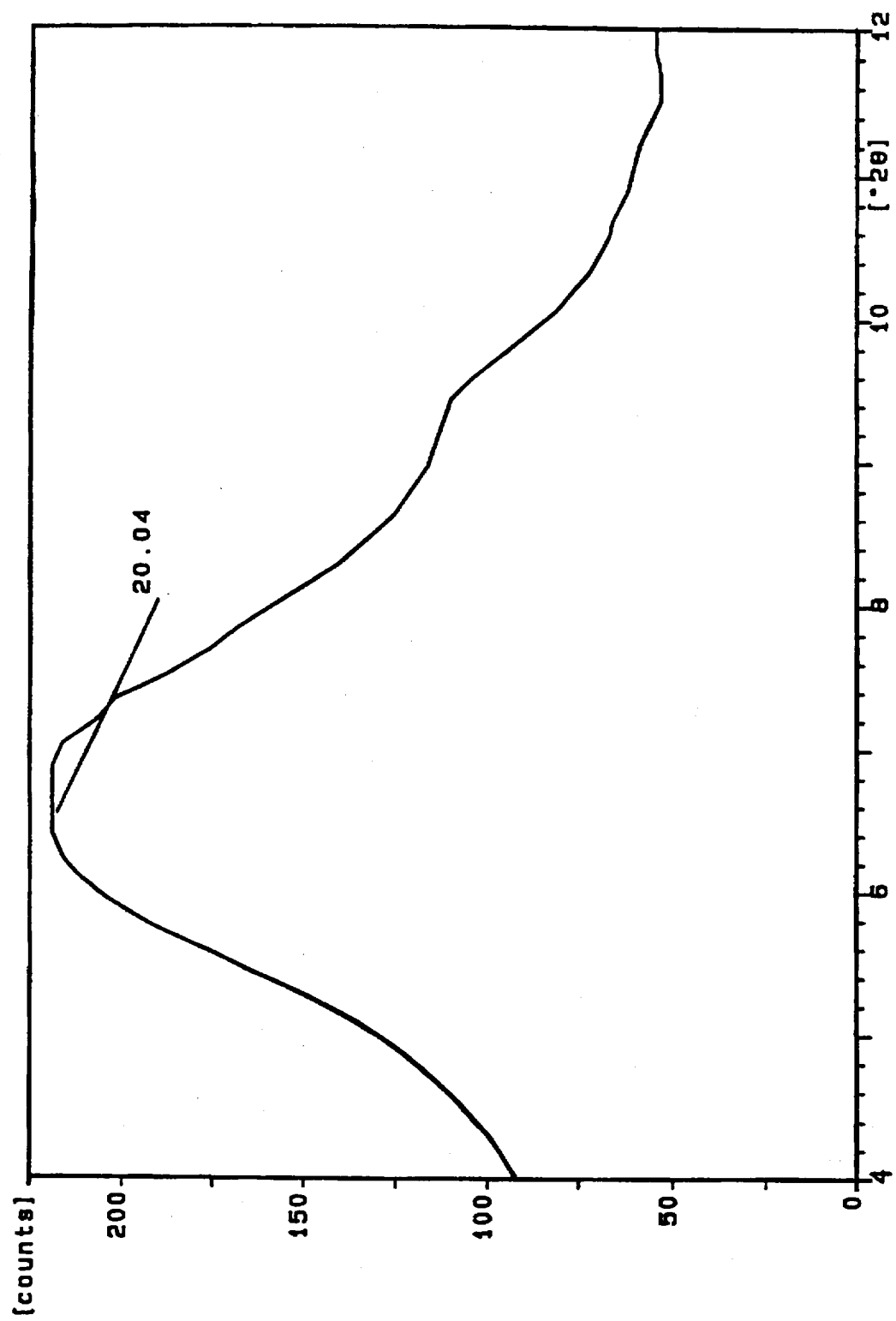
FIG. 5 is an x-ray diffraction pattern for a complex of PVOH (weight average molecular weight of 15,000):sodium montmorillonite clay, in Angstroms, at a weight ratio of PVOH:clay of 20:80.
Figure 6:
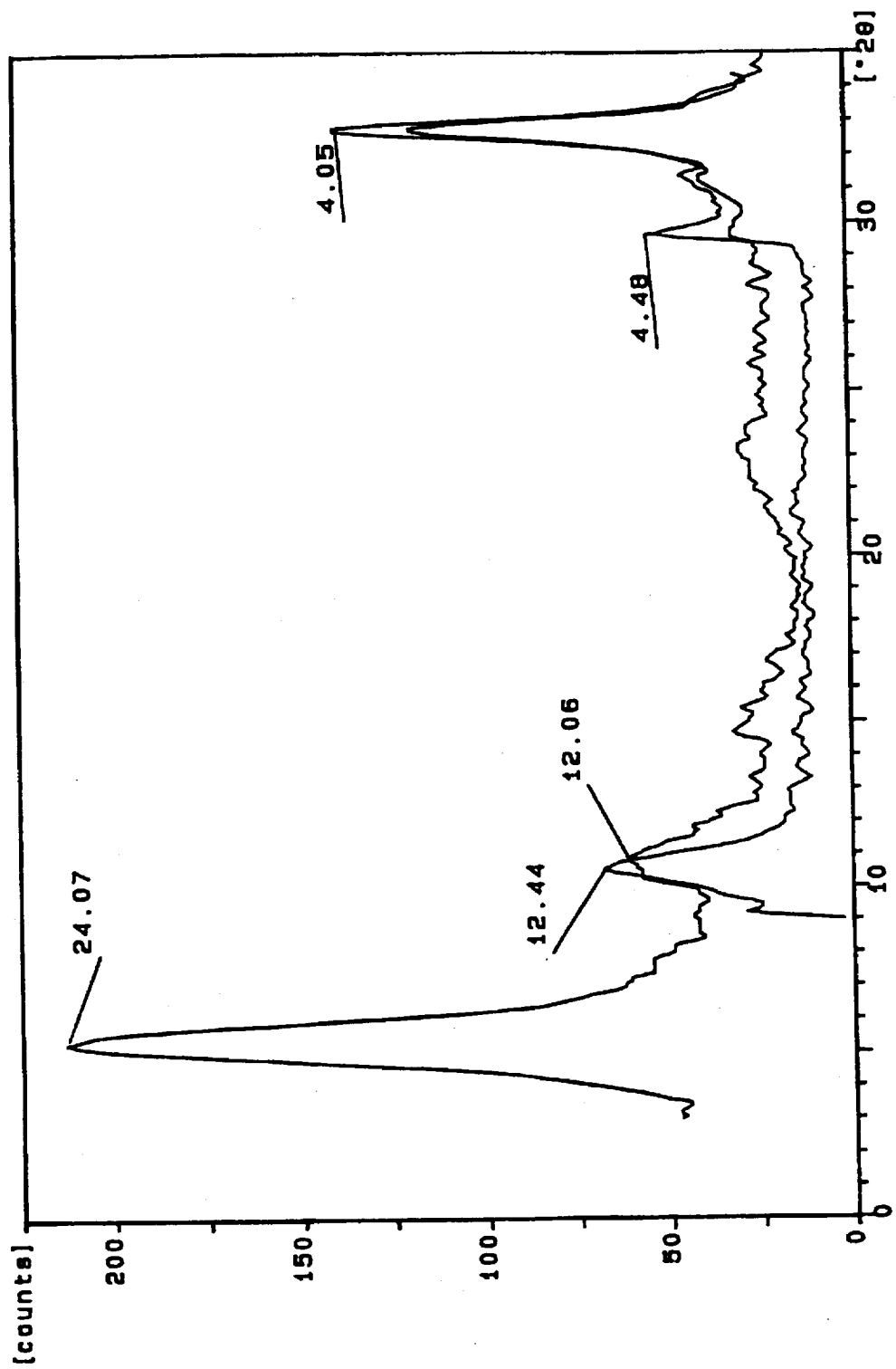
FIG. 6 is an x-ray diffraction pattern for a complex of PVP:sodium montmorillonite clay, in Angstroms, at a weight ratio of PVP:clay of 20:80 (upper pattern); and an x-ray diffraction pattern for ≈100% sodium montmorillonite clay having a crystobalite impurity (lower pattern)
Figure 7:
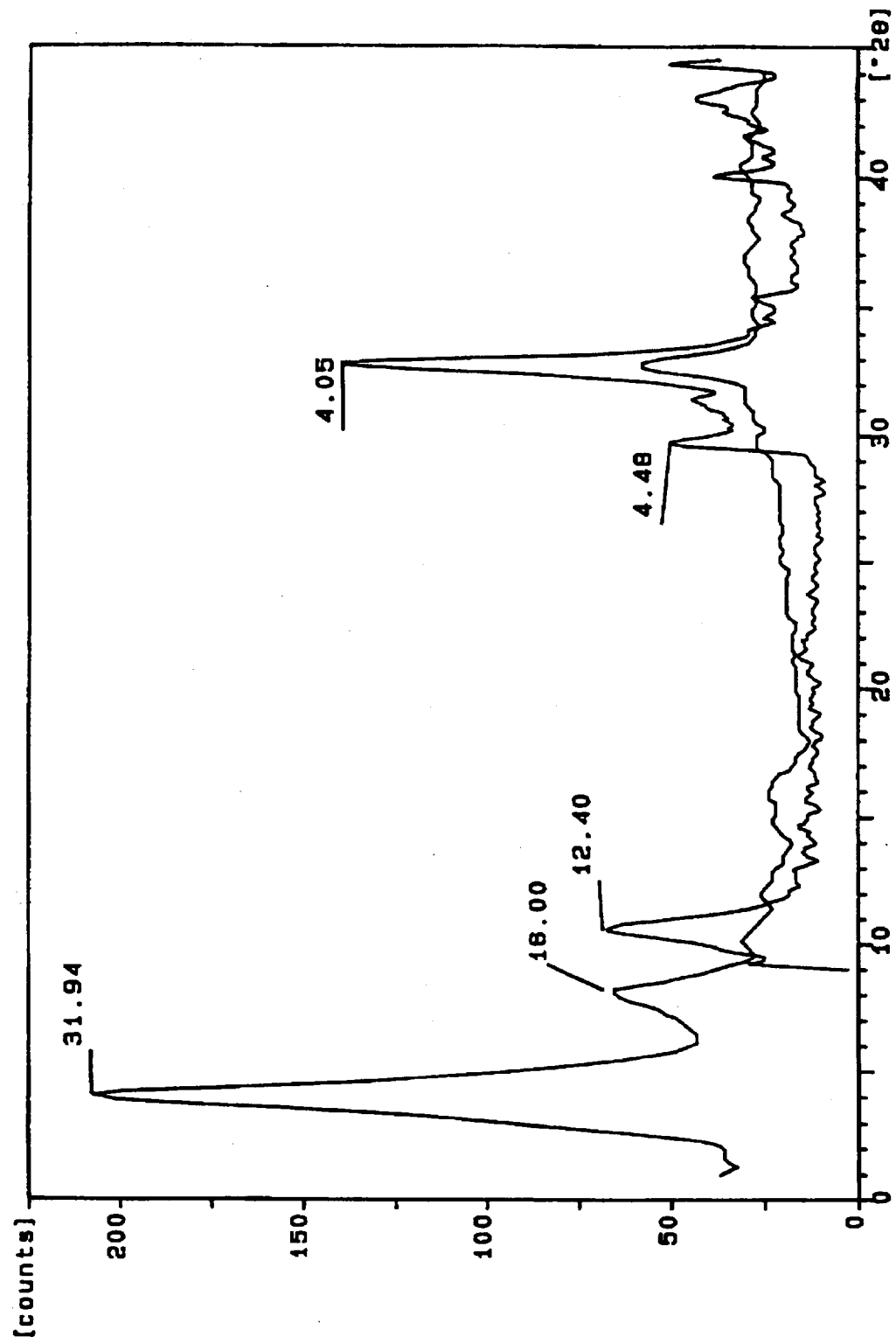
FIG. 7 is an x-ray diffraction pattern for a complex of PVP:sodium montmorillonite clay, in Angstroms, at a weight ratio of PVP:clay of 50:50 (upper pattern); and an x-ray diffraction pattern for ≈100% sodium montmorillonite clay having a crystobalite impurity (lower pattern)

The graphs of FIGS. 3 to 5 are x-ray diffraction patterns of blends of different water-soluble polymers with sodium bentonite clay. The pattern of FIGS. 3 and 4 are taken from intercalated clay 20% by weight polyvinylpyrrolidone (weight average molecular weight=10,000 for FIG. 3; 40,000 for FIG. 4) and 80% by weight sodium bentonite clay. The blends were formed by mixing the PVP and clay from a 2% solution of PVP and a 2% dispersion of sodium bentonite in a 1:4 ratio, respectively. As shown, the PVP:clay complexed since no d(001) smectite peak appears at about 12.4 Å. Similar results are shown for 20% polyvinyl alcohol, 80% sodium bentonite, as shown in FIG. 5, blended in the same way and in the same ratio. The d(001) peak of non-exfoliated (layered) sodium bentonite clay appears at about 12.4 Å, as shown in the x-ray diffraction pattern for sodium bentonite clay (containing about 10% by weight water) in the lower x-ray diffraction patterns of FIGS. 6 and 7. The graphs of FIG. 6 are x-ray diffraction patterns of sodium bentonite clay (montmorillonite) and a PVP:clay complex that was obtained by extrusion of a blend of 20% by weight polyvinylpyrrolidone (molecular weight 10,000) and 80% by weight sodium bentonite clay (containing a crystobalite impurity, having a d-spacing of about 4.05 Å) with 35% water based on the weight of dry clay plus polymer. As shown in FIG. 6, the PVP clay complexed since no d(001) smectite peak appears at about 12.4 Å. There are basal spacings with a d(001) peak of PVP:clay complex at about 24 Å and d(002) peak of PVP:clay complex at about 12 Å, that shows close to regular structure of this intercalated composite with a PVP:clay ratio equal to 1:4. The graphs of FIG. 7 are x-ray diffraction patterns of sodium bentonite clay (montmorillonite) and PVP:clay complex that was obtained by extrusion of blend of 50% by weight polyvinylpyrrolidone (molecular weight 10,000) and 50% of sodium bentonite clay (containing a crystobalite impurity, having d-spacing of about 4.05 Å) with 35% water based on the weight of dry clay plus polymer. As shown in FIG. 7, the PVP:clay complexed since no d(001) smectite peak appears at about 12.4 Å. There are basil spacings with a d(001) peak of the PVP:clay complex at about 32 Å and a d(002) peak of PVP:clay complex at about 16 Å that shows close to regular structure of this intercalated composite with a PVP-:clay ratio equal to 1:1. When mechanical blends of powdered sodium bentonite clay (containing about 10% by weight water) and powdered polyvinylpyrrolidone (PVP) polymer were mixed with water (about 75% by weight water), the polymer was intercalated between the bentonite clay platelets, and an exothermic reaction occurred that, it is theorized, resulted from the polymer being bonded to the internal faces of the clay platelets sufficiently for exfoliation of the intercalated clay.

It should be noted, also, that exfoliation did not occur unless the bentonite clay included water in an amount of at least about 4% by weight, based on the dry weight of the clay, preferably at least about 10% by weight water. The water can be included in the clay as received, or can be added to the clay prior to or during intercalant polymer contact.

It should also be noted that the exfoliation occurred without shearing—the layered clay exfoliated naturally after sufficient intercalation of polymer between the platelets of the layered bentonite—whether the intercalate was achieved by using sufficient water, e.g., at least about 20% by weight, preferably about 30% to about 100% by weight, or higher, based on the dry weight of the clay, for sufficient migration of the polymer into the interlayer spaces, and preferably also by extruding. When intercalating in a phyllosilicate slurry, it has been found that at least about 65% by weight water, based on the total weight of the intercalating composition, provides easier mixing and faster migration of the polymer into the spaces between platelets.

Figure 8:
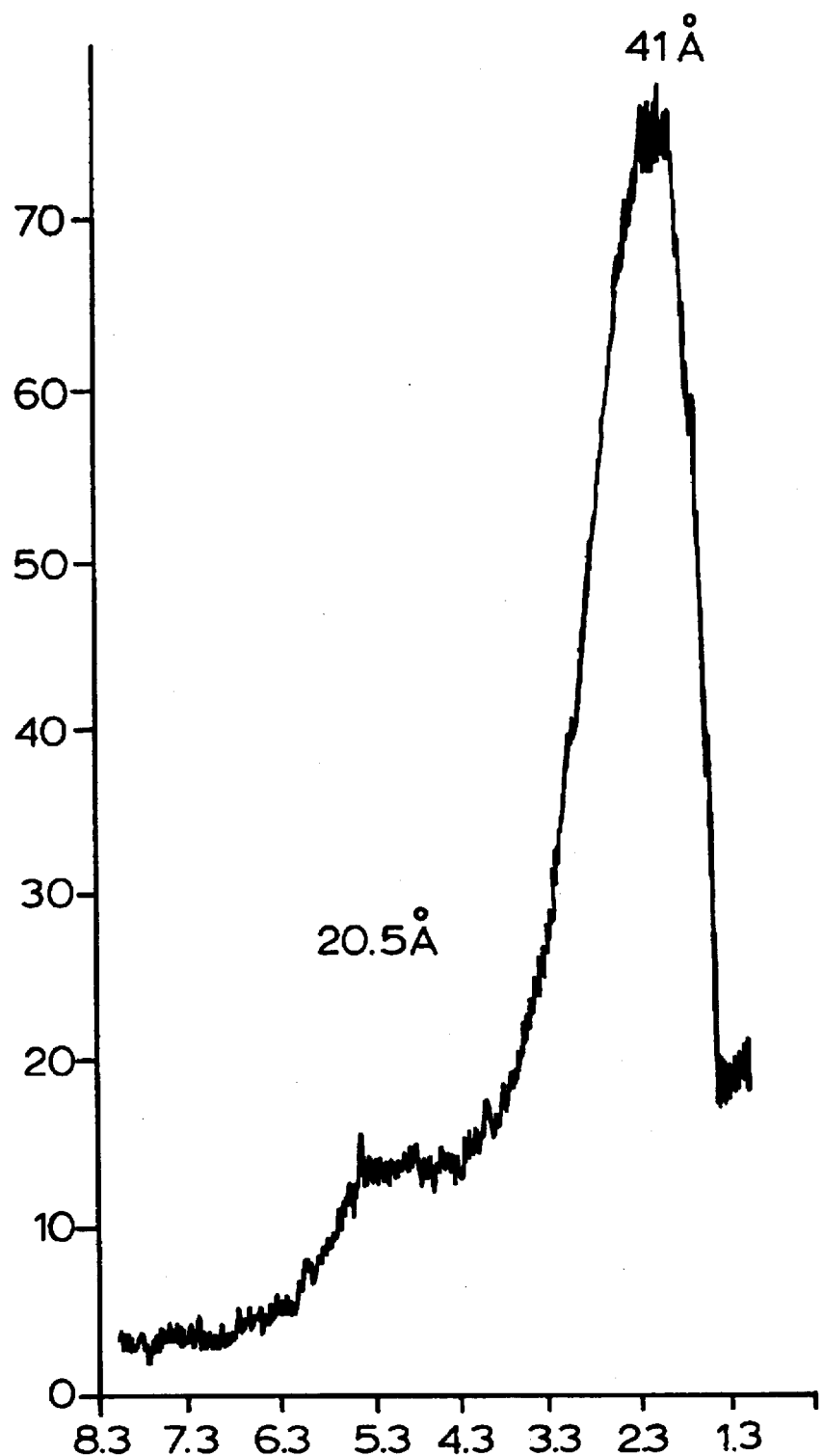
FIG. 8 is a portion of an x-ray diffraction pattern for PVP:sodium montmorillonite clay, in Angstroms, at a PVP::clay ratio of 80:20, showing a PVP:clay complex peak or d(001) spacing of about 41 Å.

The x-ray diffraction pattern of FIG. 8 shows that at a ratio of 80% PVP, 20% clay, the periodicity of the intercalated composite, with a PVP clay ratio equal to 4:1, is increased to about 41 Å.

A number of compositions were prepared containing intercalates (complexes) formed by contacting sodium bentonite clay with an intercalating composition. The intercalating composition contained clay, water and a water-soluble polymer. Sufficient sodium bentonite clay was added to the intercalating composition to provide a preferred weight ratio of dry clay/polymer of 4:1 (80% by weight clay/20% by weight polymer) with sufficient water such that the intercalating composition and clay contained 35–40% by weight water for effective extrusion of the composition through die openings of an extruder. Similarly, the polymer and water can be mixed with clay to complex (intercalate) the polymer to the platelet surfaces between adjacent clay platelets.

The complex (intercalate) was then combined with various organic liquids (with and without water) to determine the effect of intercalate loading as well as temperature, pH and water content of the intercalating composition on the viscosity of the liquid by the addition of the intercalate or exfoliate thereof. For the composition shown in FIGS. 9–14, every clay-PVP (polyvinylpyrrolidone) complex was an extruded blend having a weight ratio of clay:PVP of 4:1 containing 35–40% by weight water, based on the dry weight of the clay plus polymer. The complexes (intercalates and/or exfoliates) formed by extrusion were admixed, at various complex percentages, with the designated percentages of organic liquid (sometimes also with water) and the viscosity measured using a Brookfield viscometer, spindle #4, unless otherwise noted.

Figure 9:
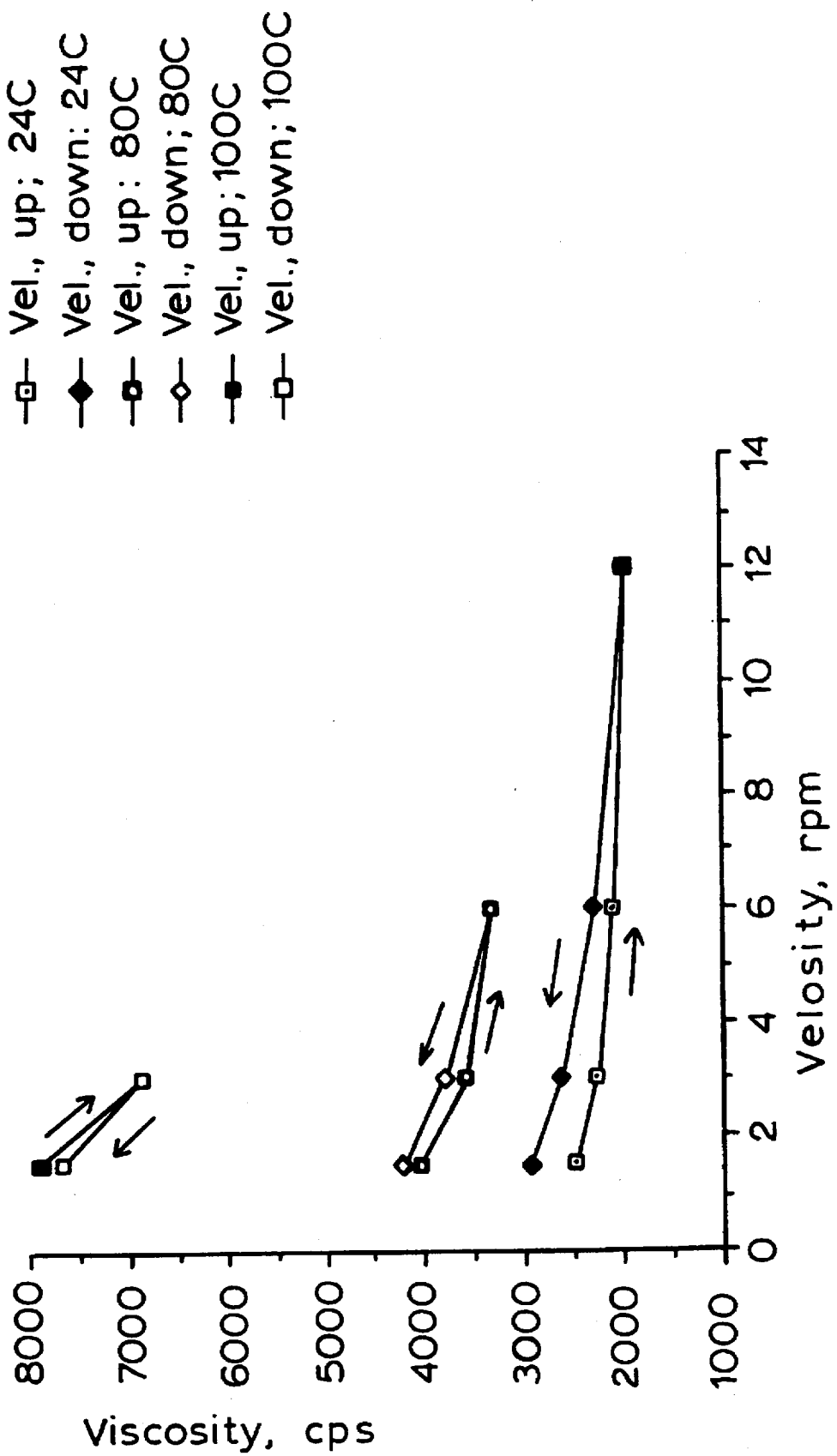
FIG. 9 is a graph of composition viscosity at 24° C. vs. spindle velosity r.p.m. for compositions of 10% by weight Na bentonite clay: polyvinylpyrrolidone (PVP) complex, 6% by weight water, and 84% by weight glycerol showing thixotropy at increased and decreased shear, and increased viscosity with increased temperatures of intercalation in formation of the clay:PVP complex.

As shown in the graph of FIG. 9, a composition consisting of 10% by weight of an extruded complex of 80% by weight sodium bentonite clay and 20% by weight polyvinylpyrrolidone (extruded using 38% water, based on the dry weight of the clay plus polymer, and then dried) was combined with 6% water and 84% glycerol. The composition was mixed to form a homegeneous composition and sometimes heated to form a more viscous gel before cooling to room temperature (24° C.) to measure the viscosity. As shown in FIG. 9, mixing 10% by weight clay:PVP intercalate into 84% glycerol, and 6% water resulted in a viscosity of 2,000–3,000 centipoises and heating the composition to gelation resulted in viscosities of about 3,500–4,000 centipoises (80° C.) and 7,000–8,000 centipoises (100° C.)—all viscosities being measured at 24° C.

Figure 10:
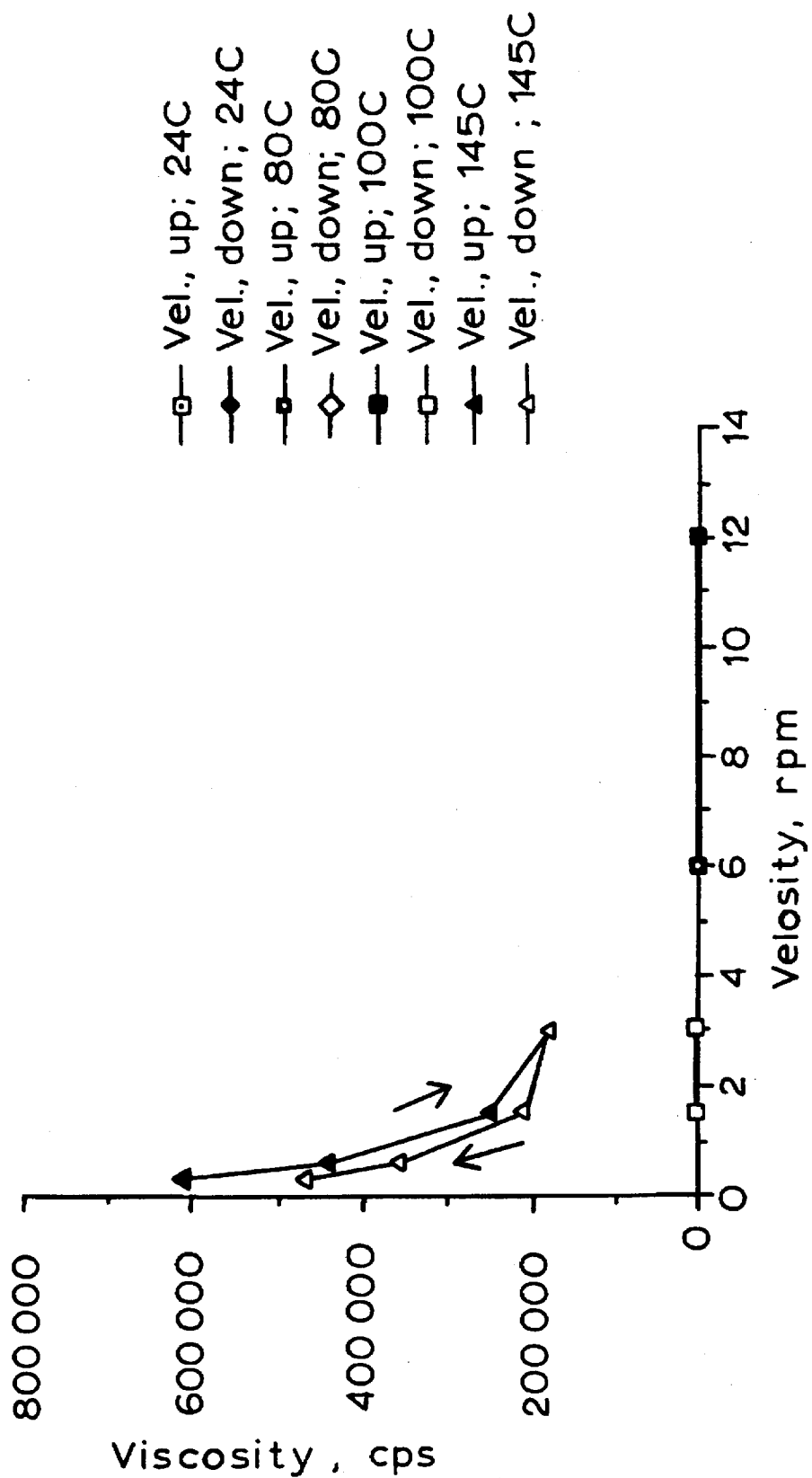
FIG. 10 is a graph similar to the graph of FIG. 9, at a different scale, showing the data from FIG. 9 along the horizontal axis, and showing an unexpected increase in viscosity achieved by heating the composition gel to a temperature of 145° C. before cooling and increasing viscosity at 24° C.

As shown in FIG. 10, when the intercalate/water/glycerol compositions of FIG. 9 were heated to 145° C. and then cooled to room temperature, the viscosity of the 10% intercalate/6% $H_2O$/84% glycerol composition was increased to about 200,000 to about 600,000 centipoises.

Figure 11:
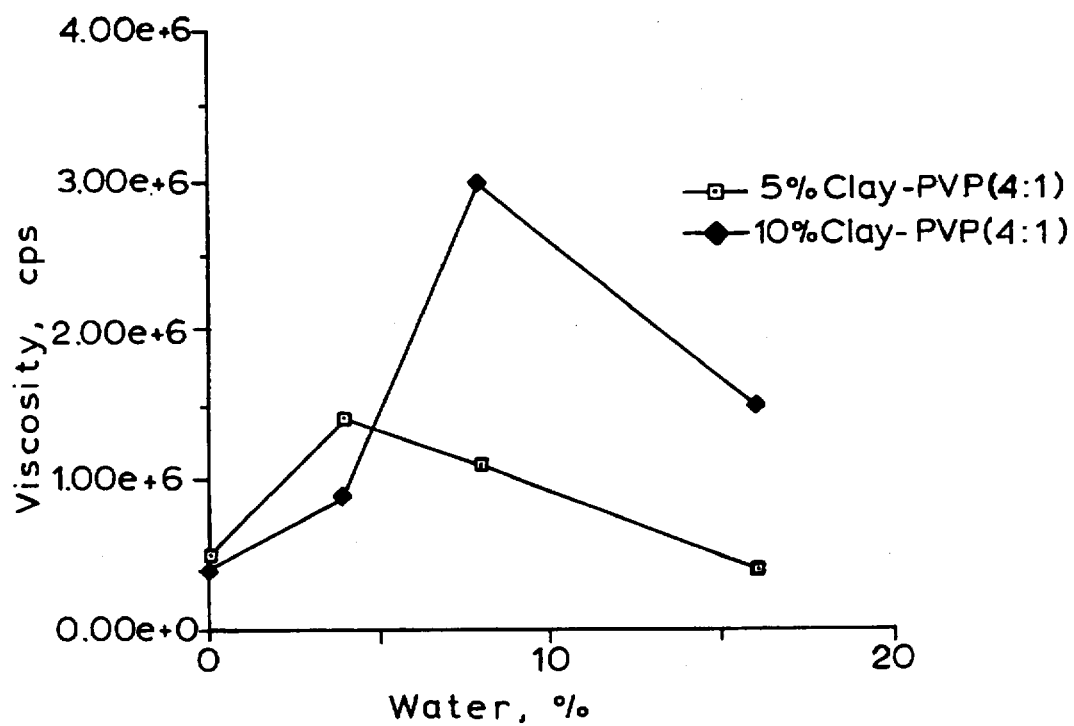
FIG. 11 is a graph of composition viscosity at 24° C. of compositions containing 5% clay:PVP complex and 10% by weight Na bentonite:PVp complex (4:1 weight ratio for both) mixed with water and glycerol with various amounts of water (water plus glycerol equals 100%) showing an increase in viscosity from about 500,000 centipoises to about 3,000,000 centipoises by increasing the water content from 0% (100% glycerol) to about 7.5% water, and a decrease in viscosity with the addition of more than 7.5% water.

FIG. 11 shows compositions similar to those of FIGS. 9 and 10 at two different loadings (5% by weight and 10% by weight) of the clay:PVP complex (again, a 4:1 weight ratio of sodium bentonite to polyvinylpyrrolidone extruded with 38% water and then dried to about 3%–10% water, preferably about 4% to 6% water) with glycerol and water, with varied amounts of water. The compositions were gelled by heating to 140° C. and the compositions were cooled to room temperature (24° C.) before the viscosity was measured. As shown in FIG. 11, for a 5% loading of the intercalate, an increase in water percentage up to about 5% by weight causes an increase in viscosity; for a 10% intercalate loading, an increase in water percentage up to about 8% by weight increases the viscosity of the intercalate/glycerol/water composition—with viscosities of about 500,000 centipoises to about 3,000,000 centipoises being achieved.

Figure 12:
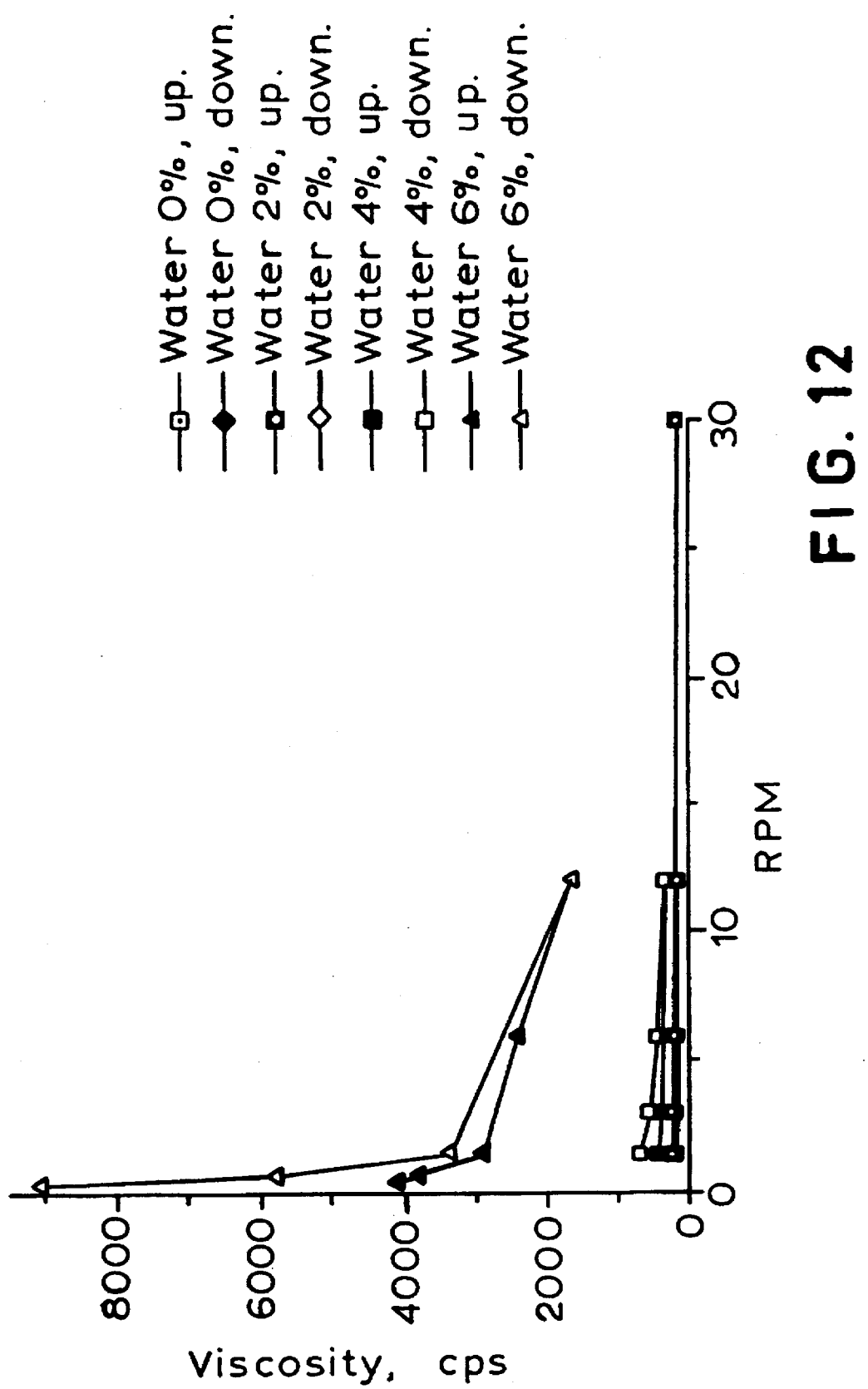
FIGS. 12 and 13 are graphs, at different scales, of composition viscosity at 24° C. of compositions containing 5% by weight Na bentonite clay: PVP complex (4:1 weight ratio); 0–6% by weight water; and 89–95% by weight ethylene glycol showing thixotropy with raising and lowering of shear (RPM) and an increase in viscosity with increased water content from 0% water to 2% water, 4% water and 6% water; and substantial increase in viscosity when the gel is heated to 85° C. before cooling to 24° C. to measure viscosity (FIG. 13)
Figure 13:
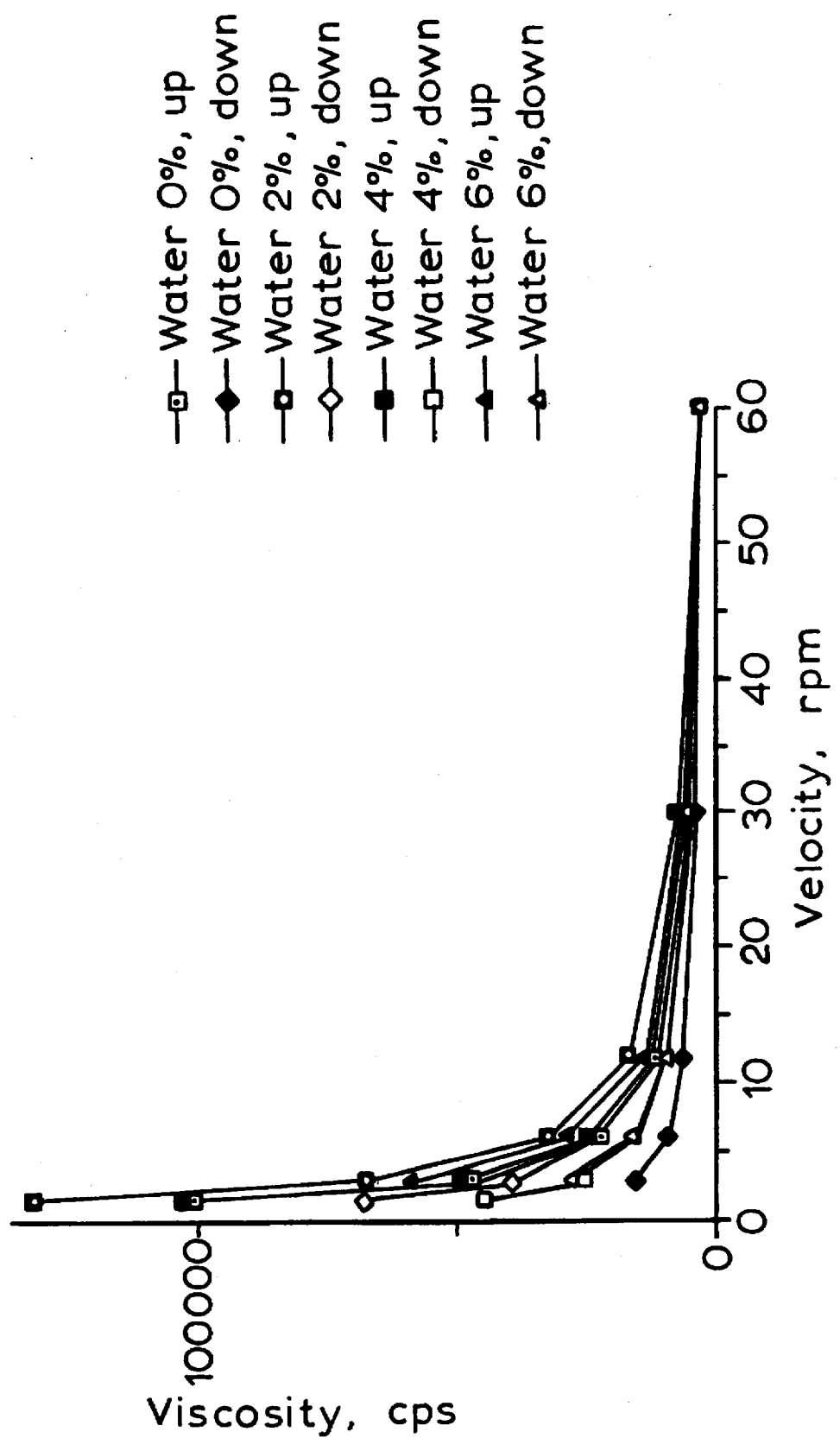

FIG. 12 is a graph showing viscosity measured at room temperature (24° C.), of compositions containing 5% by weight of the sodium bentonite clay:PVP complex (intercalate) admixed with 0–6% by weight water and 89–95% by weight ethylene glycol, without heating. As shown in FIG. 12, the addition of up to about 6% by weight water increases the viscosity of the intercalate/ethylene glycol composition-(without heating) from less than 1,000 centipoises to more than 9,000 centipoises. The same compositions were heated to 85° C. and the viscosity measured (after cooling to room temperature). The effect of temperature (85° C.) is quite dramatic, as shown in FIG. 13, increasing the viscosity to well over 100,000 centipoises, with the addition of about 2% by weight water, and increasing viscosity, substantially, without water as well.

FIG. 14 is a graph showing viscosity, again measured at room temperature (24° C.) of an unheated mixture of 10% by weight sodium bentonite clay:PVP complex (intercalate), with the remainder being varied percentages of ethanol and water. As shown in FIG. 14, for ethanol, the addition of up to about 20% by weight water (70% ethanol, 10% clay:PVP complex) increases the viscosity of the composition from well below 400,000 centipoises to about 1,000,000 centipoises, even without heating.

Various other organic liquids were admixed with clay-:polymer intercalates at varied percentages of intercalate and varied percentages of water. All experiments used a 4:1 weight ratio of sodium bentonite clay to polyvinylpyrrolidone either mixed with a water slurry of the clay and polymer at 5–80% water—Technique #1) and then dried; or extruded with 35–38% water and then dried (Technique #2). The results are shown in the following examples:

EXAMPLE 1

2-PROPANOL WITH 10%-4:1 COMPLEX (CLAY:PVP)
10%-4:1 Complex (20 grams) 27%-Water (54 grams)
63%-2-Propanol (126 grams) TECHNIQUE #1
Spindle: #1

| RPM | 3 | 6 | 12 |
|---|---|---|---|
| Viscosity (cps) | 762 | 393 | 234 |

EXAMPLE 2

8% Water (16 grams) 5%-4:1 Complex (10 grams)
87% Propylene Glycol (174 grams) TECHNIQUE #1
Spindle: #4   Was heated to 160° C.

| RPM | 3 | 6 | 12 |
|---|---|---|---|
| Viscosity (cps) | 23,800 | 11,700 | 7,700 |

EXAMPLE 3

8% Water (16 grams) 5%-4:1 Complex (10 grams)
87% Propylene Glycol (174 grams) TECHNIQUE #2
Spindle: #4   Was heated to 160° C.

| RPM | 3 | 6 | 12 |
|---|---|---|---|
| Viscosity (cps) | 23,600 | 9,100 | 5,600 |

EXAMPLE 4

8% Water (16 grams) 10%-4:1 Complex (20 grams)
82% Propylene Glycol (164 grams) TECHNIQUE #1
Spindle: #4   Was heated to 115–120° C.

| RPM | 3 | 6 | 12 |
|---|---|---|---|
| Viscosity (cps) | 21,400 | 11,700 | 7,350 |

EXAMPLE 5

8% Water (16 grams) 10%-4:1 Complex (20 grams)
82% Propylene Glycol (164 grams) TECHNIQUE #2
Spindle: #4   Was heated to 115–120° C.

| RPM | 3 | 6 | 12 |
|---|---|---|---|
| Viscosity (cps) | 19,000 | 10,600 | 6,950 |

Propylene glycol, glycerol, propanol, acetone, and anhydrous alcohol were mixed with varied percentages of sodium bentonite clay:PVP complexes, either slurried or extruded with water and then dried, and varied percentages of water, as shown in the following Examples.

EXAMPLE 6

Propylene Glycol Gel

| % of Complex | % of Water | Syneresis |
|---|---|---|
| 20 | 8 | None |

EXAMPLE 7

Propylene Glycol Gel

| % of Complex | % of Water | Syneresis |
|---|---|---|
| 15 | 8 | None |
| 15 | 24 | None |

EXAMPLE 8

Propylene Glycol Gel

| % of Complex | % of Water | Syneresis |
|---|---|---|
| 10 | 4 | None |
| 10 | 6 | None |
| 10 | 8 | None |
| 10 | 16 | None |
| 10 | 24 | None |

EXAMPLE 9

Propylene Glycol Gel

| % of Complex | % of Water | Syneresis |
|---|---|---|
| 5 | 4 | Very Little |
| 5 | 8 | Very Little |
| 5 | 16 | Very Little |
| 5 | 24 | None |
| 5 | 30 | None |

EXAMPLE 10

Propylene Glycol Gel

| % of Complex | % of Water | Syneresis |
|---|---|---|
| 2.5 | 4 | Very Little |
| 2.5 | 8 | None |
| 2.5 | 12 | None |
| 2.5 | 16 | None |
| 2.5 | 24 | None |

EXAMPLE 11

Glycerol Gel

| % of Complex | % of Water | Syneresis |
|---|---|---|
| 10 | 0 | None |
| 10 | 4 | None |

-continued

Glycerol Gel

| % of Complex | % of Water | Syneresis |
|---|---|---|
| 10 | 8 | None |
| 10 | 16 | None |

EXAMPLE 12

Glycerol Gel

| % of Complex | % of Water | Syneresis |
|---|---|---|
| 5 | 0 | None |
| 5 | 2 | None |
| 5 | 4 | None |
| 5 | 8 | None |

EXAMPLE 13

Ethylene Glycol Gel

| % of Complex | % of Water | Syneresis |
|---|---|---|
| 10 | 8 | None |
| 10 | 16 | None |

EXAMPLE 14

Ethylene Glycol Gel

| % of Complex | % of Water | Syneresis |
|---|---|---|
| 5 | 0 | Very Little |
| 5 | 2 | None |
| 5 | 4 | None |
| 5 | 6 | None |

EXAMPLE 15

Alcohol, Anydrous Reagent - 9401-03

| % of Complex | % of Water | Syneresis |
|---|---|---|
| 10 | 4 | Very Much |
| 10 | 8 | Yes |
| 10 | 16 | None |

EXAMPLE 16

1,4 Butane Diol Gel

| % of Complex | % of Water | Syneresis |
|---|---|---|
| 10 | 4 | None |

EXAMPLE 17

1,4 Butane Diol Gel

| % of Complex | % of Water | Syneresis |
|---|---|---|
| 5 | 4 | Very Little |
| 5 | 8 | None |
| 5 | 16 | None |

EXAMPLE 18

1-Propanol Gel

| % of Complex | % of Water | Syneresis |
|---|---|---|
| 10 | 8 | Yes |
| 10 | 27 | Yes |
| 10 | 45 | Yes |
| 10 | 50 | None |

EXAMPLE 19

Acetone Gel

| % of Complex | % of Water | Syneresis |
|---|---|---|
| 20 | 40 | None |

EXAMPLE 20

Acetone Gel

| % of Complex | % of Water | Syneresis |
|---|---|---|
| 10 | 16 | Yes |
| 10 | 45 | None |
| 10 | 50 | None |

EXAMPLE 21

10% Complex, 8% Water, 72% Propylene Glycol (Master Gel)
Spindle: #4

| RPM | 0.3 | 0.6 | 1.5 |
|---|---|---|---|
| Viscosity (cps) | 464,000 | 306,000 | 162,800 |

EXAMPLE 22

27.5% Master Gel of Example 21
65% Silicone Oil, 0.75% Abil*, 6.75% Water
Spindle: #4

| RPM | 0.3 | 0.6 | 1.5 |
|---|---|---|---|
| Viscosity (cps) | 1,630,000 | EEE** | EEE** |

* Abil: Amino silane surfactant from Hüls America
** EEE — Exceeded capacity of viscometer

EXAMPLE 23

| 15% Complex, 24% Water, 61% Propylene Glycol (Master Gel) Spindle: #4 | | | |
|---|---|---|---|
| RPM | 0.3 | 0.6 | 1.5 |
| Viscosity (cps) | 456,000 | 278,000 | 142,400 |

EXAMPLE 24

| 27.5% Master Gell of Example 23 65% Silicone Oil, 0.75% Abil, 6.75% Water Spindle: #4 | | | |
|---|---|---|---|
| RPM | 0.3 | 0.6 | 1.5 |
| Viscosity (cps) | 1,000,000 | 625,000 | 361,200 |

EXAMPLE 25

| 15% Complex, 8% Water, 77% Propylene Glycol (Master Gel) Spindle: #4 | | | |
|---|---|---|---|
| RPM | 0.3 | 0.6 | 1.5 |
| Viscosity (cps) | 168,000 | 63,000 | 40,800 |

EXAMPLE 26

| 27.5% Master Gel of Example 25 65% Silicone Oil, 0.75% Abil, 6.75% Water Spindle: #4 | | | |
|---|---|---|---|
| RPM | 0.3 | 0.6 | 1.5 |
| Viscosity (cps) | 1,630,000 | 981,000 | EEE* |

*EEE — Exceeded capacity of ter

EXAMPLE 27

| 10% Complex, 0% Water, 90% Glycerol (Master Gel) Spindle: #4 | | | |
|---|---|---|---|
| RPM | 0.3 | 0.6 | 1.5 |
| Viscosity (cps) | EEE* | EEE* | EEE* |

*EEE — Exceeded Capacity of viscometer

EXAMPLE 28

| 10% Complex, 4% Water, 85% Glycerol (Master Gel) Spindle: #4 | | | |
|---|---|---|---|
| RPM | 0.3 | 0.6 | 1.5 |
| Viscosity (cps) | 240,000 | 137,000 | 114,000 |

EXAMPLE 29

| 37.5% - Master Gel of Example 27, 51% Silicone Oil, 1.0% Abil, 11% Water Spindle: #4 | | | |
|---|---|---|---|
| RPM | 0.3 | 0.6 | 1.5 |
| Viscosity (cps) | 376,000 | 308,000 | 180,400 |

EXAMPLE 30

| 37.5% - Master Gel of Example 28, 51% Silicone Oil, 1.0% Abil, 11% Water Spindle: #4 | | | |
|---|---|---|---|
| RPM | 0.3 | 0.6 | 1.5 |
| Viscosity (cps) | 512,000 | 371,000 | 201,600 |

EXAMPLE 31

| 37.5% - Master Gel of Example 28, 55% Silicone Oil, 1% Abil, 6.5% Water Spindle: #4 | | | |
|---|---|---|---|
| RPM | 0.3 | 0.6 | 1.5 |
| Viscosity (cps) | 1,164,000 | 699,000 | EEE* |

*EEE — Exceeded capacity of viscometer

EXAMPLE 32

| 34% Master Gel of Example 28, 60% Silicone Oil, 1.0% Abil, 5% Water Spindle: #4 | | | |
|---|---|---|---|
| RPM | 0.3 | 0.6 | 1.5 |
| Viscosity (cps) | EEE* | EEE* | EEE* |

*EEE — Exceeded capacity of viscometer

EXAMPLE 33

| 10% Complex (20 grams), 4% Water (8 grams), 91% Propylene Glycol (182 grams) Spindle: #4 | | | |
|---|---|---|---|
| RPM | 3 | 6 | 12 |
| Viscosity (cps) | 16,200 | 10,500 | 7,550 |

EXAMPLE 34

| 10% Complex (20 grams), 6% Water (12 grams,) 84% Propylene Glycol (168 grams) Spindle: #4 | | | |
|---|---|---|---|
| RPM | 3 | 6 | 12 |
| Viscosity (cps) | 22,200 | 15,300 | 12,000 |

EXAMPLE 35

10% Complex (20 grams), 8% Water (16 grams),
82% Propylene Glycol (164 grams)
Spindle: #4

| RPM | 3 | 6 | 12 |
|---|---|---|---|
| Viscosity (cps) | 14,400 | 12,100 | 9,400 |

EXAMPLE 36

10% Complex (20 grams), 16% Water (32 grams),
74% Propylene Glycol (148 grams)
Spindle: #4

| RPM | 3 | 6 | 12 |
|---|---|---|---|
| Viscosity (cps) | 12,000 | 10,600 | 7,500 |

EXAMPLE 37

10% Complex (20 grams), 24% Water (48 grams),
66% Propylene Glycol (132 grams)
Spindle: #4

| RPM | 3 | 6 | 12 |
|---|---|---|---|
| Viscosity (cps) | 22,400 | 13,100 | 8,650 |

EXAMPLE 38

4% Water (8 grams), 1.25% Complex 4:1 (2.5 grams),
94.75% Propylene Glycol (189.5 grams) - Was heated to 170° C.
Spindle: #2

| RPM | 3 | 6 | 12 |
|---|---|---|---|
| Viscosity (cps) | 290 | 285 | 227.5 |

EXAMPLE 39

8% Water (16 grams), 1.25% Complex 4:1 (2.5 grams),
90.75% Propylene Glycol (181.5 grams) - Was heated to 160–165° C.
Spindle: #2

| RPM | 3 | 6 | 12 |
|---|---|---|---|
| Viscosity (cps) | 510 | 420 | 385 |

EXAMPLE 40

12% Water (24 grams), 1.25% Complex 4:1 (2.5 grams),
86.75% Propylene Glycol (173.5 grams) - Was heated to 165–170° C.
Spindle: #2

| RPM | 3 | 6 | 12 |
|---|---|---|---|
| Viscosity (cps) | 4,500 | 3,135 | 1,897.5 |

EXAMPLE 41

16% Water (32 grams), 1.25% Complex 4:1 (2.5 grams),
82.75% Propylene Glycol (165.5 grams) - Was geated to 170° C.
Spindle: #2

| RPM | 3 | 6 | 12 |
|---|---|---|---|
| Viscosity (cps) | 5,370 | 3,350 | 1,970 |

EXAMPLE 42

4% Water (8 grams), 5% Complex (10 grams),
91% Propylene Glycol (182 grams) - Heated to 110° C. - From
110 to 155° C. took 15 min. - Max. temp. = 160° C.
Spindle: #2

| RPM | 12 | 30 | 60 |
|---|---|---|---|
| Viscosity (cps) | 112.5 | 94.0 | 91.5 |

EXAMPLE 43

4% Water (8 grams), 5% Complex (10 grams),
91% Propylene Glycol (182 grams) - Heated to 110° C. - From
110 to 155° C. took 15 min. - Max. temp. = 160° C.
Spindle: #4

| RPM | 1.5 | 3 | 6 | 12 |
|---|---|---|---|---|
| Viscosity (cps) | 78,000 | 36,600 | 21,200 | 11,950 |

EXAMPLE 44

8% Water (16 grams), 5% Complex (10 grams),
87% Propylene Glycol (174 grams) - Heated to 150° C. - From
110 to 150° C. took 20 min. - Max. temp. = 150° C.
Spindle: #2

| RPM | 12 | 30 | 60 |
|---|---|---|---|
| Viscosity (cps) | 145.0 | 130.0 | 120.5 |

EXAMPLE 45

16% Water (32 grams), 5% Complex (10 grams),
79% Propylene Glycol (158 grams) - Heated to 145–150° C. - From
110 to 150° C. took 19 min. - Max. temp. = 150° C.
Spindle: #2

| RPM | 30 | 60 |
|---|---|---|
| Viscosity (cps) | 98.0 | 102.5 |

EXAMPLE 46

16% Water (32 grams), 5% Complex (10 grams),
79% Propylene Glycol (158 grams) - Heated to 145–150° C. - From
110 to 150° C. took 19 min. - Max. temp. = 150° C.
Spindle: #4

| RPM | 1.5 | 3 | 6 | 12 |
|---|---|---|---|---|
| Viscosity (cps) | 16,000 | 9,000 | 7,800 | 5,700 |

EXAMPLE 47

16% Water (32 grams), 5% Complex (10 grams),
79% Propylene Glycol (158 grams) - Heated to 145–150° C. - From
110 to 150° C. took 19 min. - Max. temp. = 150° C.
Spindle: #3

| RPM | 6 | 12 | 30 |
|---|---|---|---|
| Viscosity (cps) | 7,220 | 5,110 | 3,040 |

EXAMPLE 48

24% Water (48 grams), 5% Complex (10 grams),
71% Propylene Glycol (142 grams) - Heated to 120° C. - From
110 to 125° C. took 19 min. - Max. temp. = 125° C.
Spindle: #2

| RPM | 30 | 60 |
|---|---|---|
| Viscosity (cps) | 118.0 | 108.0 |

EXAMPLE 49

24% Water (48 grams), 5% Complex (10 grams),
71% Propylene Glycol (142 grams) - Heated to 120° C. - From
110 to 125° C. took 19 min. - Max. temp. = 125° C.
Spindle: #4

| RPM | 1.5 | 3 | 6 | 12 |
|---|---|---|---|---|
| Viscosity (cps) | 8,800 | 6,600 | 5,000 | 2,800 |

EXAMPLE 50

24% Water (48 grams), 5% Complex (10 grams),
71% Propylene Glycol (142 grams) - Heated to 120° C. - From
110 to 125° C. took 19 min. - Max. temp. = 125° C.
Spindle: #3

| RPM | 6 | 12 | 30 |
|---|---|---|---|
| Viscosity (cps) | 3,820 | 2,470 | 1,100 |

EXAMPLE 51

30% Water (60 grams), 5% Complex (10 grams),
65% Propylene Glycol (130 grams) - Heated to 120° C. - From
110 to 125° C. 19 min. - Max. temp. = 125° C.
Spindle: #2

| RPM | 12 | 30 | 60 |
|---|---|---|---|
| Viscosity (cps) | 692.5 | 389.0 | 258.0 |

EXAMPLE 52

30% Water (60 grams), 5% Complex (10 grams),
65% Propylene Glycol (130 grams) - Heated to 120° C. - From
110 to 125° C. 19 min. - Max. temp. = 125° C.
Spindle: #4

| RPM | 1.5 | 3 | 6 | 12 |
|---|---|---|---|---|
| Viscosity (cps) | 23,600 | 11,200 | 5,400 | 2,800 |

EXAMPLE 53

30% Water (60 grams), 5% Complex (10 grams),
65% Propylene Glycol (130 grams) - Heated to 120° C. - From
110 to 125° C. 19 min. - Max. temp. = 125° C.
Spindle: #3

| RPM | 6 | 12 | 30 |
|---|---|---|---|
| Viscosity (cps) | 6,100 | 3,550 | 2,112 |

EXAMPLES 54

8% Water (16 grams), 5% Complex (10 grams),
87% Methanol (174 grams)
Spindle: #1

| RPM | 0.3 | 0.6 | 1.5 |
|---|---|---|---|
| Viscosity (cps) | 1,160 | 960 | 588 |

EXAMPLE 55

4% Water (8 grams), 10% - 1:4 Complex (20 grams),
86% Propylene Glycol (172 grams)
Spindle: #3

| RPM | 0.3 | 0.6 |
|---|---|---|
| Viscosity (cps) | 19,600 | 18,400 |

EXAMPLE 56

6% Water (12 grams), 10% - 1:4 Complex (20 grams),
84% Propylene Glycol (168 grams)
Spindle: #3

| RPM | 0.3 | 0.6 |
|---|---|---|
| Viscosity (cps) | 128,000 | 67,200 |

EXAMPLE 57

8% Water (16 grams), 10% - 1:4 Complex (20 grams),
82% Propylene Glycol (164 grams)
Spindle: #3

| RPM | 0.3 | 0.6 |
|---|---|---|
| Viscosity (cps) | 61,200 | 56,600 |

EXAMPLE 58

16% Water (32 grams), 10% - 1:4 Complex (20 grams),
74% Propylene Glycol (148 grams)
Spindle: #3

| RPM | 0.3 | 0.6 |
|---|---|---|
| Viscosity (cps) | 79,200 | 49,200 |

EXAMPLE 59

| | 24% Water (48 grams), 10% - 1:4 Complex (20 grams), 66% Propylene Glycol (132 grams) Spindle: #3 | |
|---|---|---|
| RPM | 0.3 | 0.6 |
| Viscosity (cps) | 168,400 | 89,000 |

EXAMPLE 60

| | 8% Water (16 grams), 5% Complex (10 grams), 87% Methanol (174 grams) Spindle: #2 | | |
|---|---|---|---|
| RPM | 0.3 | 0.6 | 1.5 |
| Viscosity (cps) | 1,160 | 960 | 588 |

EXAMPLE 61

| | 8% Water (16 grams), 5% Complex (10 grams) 87% Methanol (174 grams) Spindle: #2 | | |
|---|---|---|---|
| RPM | 6 | 12 | 30 |
| Viscosity (cps) | 280 | 160 | 80 |

EXAMPLE 62

| | 16% Water (32 grams), 5% Complex (10 grams), 79% Methanol (158 grams) Spindle: #1 | | |
|---|---|---|---|
| RPM | 0.3 | 0.6 | 1.5 |
| Viscosity (cps) | 9,860 | 5,940 | 2,232 |

EXAMPLE 63

| | 16% Water (32 grams), 5% Complex (10 grams), 79% Methanol (158 grams) Spindle: #2 | | |
|---|---|---|---|
| RPM | 6 | 12 | 30 |
| Viscosity (cps) | 665 | 403 | 204 |

EXAMPLE 64

| | 20% Water (40 grams), 5% Complex (10 grams), 75% Methanol (150 grams) Spindle: #1 | | |
|---|---|---|---|
| RPM | 0.3 | 0.6 | 1.5 |
| Viscosity (cps) | 13,880 | 7,460 | 3,228 |

EXAMPLE 65

| | 20% Water (40 grams), 5% Complex (10 grams), 75% Methanol (150 grams) Spindle: #2 | | |
|---|---|---|---|
| RPM | 6 | 12 | 30 |
| Viscosity (cps) | 905 | 455 | 244 |

EXAMPLE 66

| | 27% Water (54 grams), 5% Complex (10 grams), 68% Methanol (136 grams) Spindle: #2 | | |
|---|---|---|---|
| RPM | 0.3 | 0.6 | 1.5 |
| Viscosity (cps) | 17,400 | 10,250 | 4,640 |

EXAMPLE 67

| | 27% Water (54 grams), 5% Complex (10 grams) 68% Methanol (136 grams) Spindle: #2 | | |
|---|---|---|---|
| RPM | 6 | 12 | 30 |
| Viscosity (cps) | 1,170 | 533 | 271 |

EXAMPLE 68

| | 35% Water (70 grams), 5% Complex (20 grams), 60% Methanol (120 grams) Spindle: #2 | | |
|---|---|---|---|
| RPM | 0.3 | 0.6 | 1.5 |
| Viscosity (cps) | 16,900 | 8,900 | 3,680 |

EXAMPLE 69

| | 35% Water (70 grams), 5% Complex (20 grams), 60% Methanol (120 grams) Spindle: #2 | | |
|---|---|---|---|
| RPM | 6 | 12 | 30 |
| Viscosity (cps) | 1,175 | 525 | 251 |

Propylene glycol and glycerol gels, prepared from a 4:1 weight ratio sodium bentonite clay:PVP intercalates at a 10% by weight intercalate loading, were tested to determine if the gels could hold substantial quantities of hydrophobic silicone oil material in a stable, viscous thixotropic gel (Examples 70–76). It was found that to avoid syneresis (liquid separation) when incorporating both very hydrophobic (silicone oil) and hydrophilic (glycol or glycerol) liquids, a small amount of surfactant, e.g., an amino silane, may be included. The following examples show that viscous gels (of both hydrophobic and hydrophilic liquids) can be prepared without syneresis. The compositions of Examples 70–76 have been stable for six months and remain stable.

EXAMPLE 70

| 27.5% | 15% Propylene Glycol Gel w/8% Water |
| --- | --- |
| 65% | Silicone Oil |
| 0.75% | Abil Surfactant |
| 1.75% | Water |
| None | Syneresis |

EXAMPLE 71

| 27.5% | 15% Propylene Glycol Gel w/24% Water |
| --- | --- |
| 65% | Silicone Oil |
| 0.75% | Abil Surfactant |
| 1.75% | Water |
| None | Syneresis |

EXAMPLE 72

| 27.5% | 20% Propylene Glycol Gel w/8% Water |
| --- | --- |
| 65% | Silicone Oil |
| 0.75% | Abil Surfactant |
| 1.75% | Water |
| None | Syneresis |

EXAMPLE 73

| 37% | 10% Glycerol Gel w/0% Water |
| --- | --- |
| 51% | Silicone Oil |
| 1.0% | Abil Surfactant |
| 11% | Water |
| None | Syneresis |

EXAMPLE 74

| 34% | 10% Glycerol Gel w/4% Water |
| --- | --- |
| 60% | Silicone Oil |
| 1.0% | Abil Surfactant |
| 5% | Water |
| None | Syneresis |

EXAMPLE 75

| 37.5 | 10% Glycerol Gel w/4% Water |
| --- | --- |
| 55% | Silicone Oil |
| 1.0% | Abil Surfactant |
| 6.5% | Water |
| None | Syneresis |

EXAMPLE 76

| 37% | 10% Glycerol Gel w/4% Water |
| --- | --- |
| 51% | Silicone Oil |
| 1.0% | Abil Surfactant |
| 11% | Water |
| None | Syneresis |

The following compositions were prepared to show the viscosity increasing effect of a pH substantially outside of the 6–10, near-neutral range. A composition containing a Na bentonite:PVP complex (4:1 weight ratio clay:PVP) at 7–10% by weight; propylene glycol at 58–66% by weight, and water at 22–26% by weight, with the addition of 5–6% by weight of a 50% active aqueous solution of NaOH to pH 12–13 resulted in a thixotropic gel having a viscosity at 24° C. of 1,500,000 centipoises, without heating. The compositions were prepared by shearing all components except the NaOH in a blender for 3 minutes, then adding the NaOH and shearing for an additional 1 minute. By changing the NaOH to $H_2O$ ratio to get an optimum pH, an effective hair waving lotion/hair straightener can be obtained at high pH which can be maintained on the hair without running down auto the scalp.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A composition comprising exfoliated platelets of an intercalate, together with an organic solvent, said organic solvent present in the composition in an amount in the range of about 10% to about 99.95% by weight of the composition, said exfoliated platelets of said intercalate formed by contacting a layered silicate material, having a moisture content of at least about 4% by weight, with an intercalant polymer having a functionality selected from the group consisting of an aromatic ring; carbonyl; carboxyl; hydroxyl; amine; amide; ether; ester; an $SO_x$; a $PO_x$ structure and mixtures thereof, wherein x=2, 3, or 4 to form an intercalating composition, having a weight ratio of polymer to layered material of at least 1:20, to achieve complexing of the polymer between adjacent spaced layers of the layered silicate material from about 8 grams of polymer per 100 grams of the layered silicate material to about 90 grams of polymer per 100 grams of the layered silicate material, without an onium ion or silane coupling agent, to expand the spacing between a predominance of the adjacent platelets of said layered silicate material to at least about 5 Å, when measured after sorption of the intercalant polymer and drying to a maximum of 5% by weight water, and exfoliating a predominance of said spaced phyllosilicate platelets.

2. A composition in accordance with claim 1, wherein the concentration of intercalant polymer in said intercalating composition is at least about 0.1% by weight, based on the weight of water and polymer in the intercalating composition.

3. A composition in accordance with claim 2, wherein the concentration of intercalant polymer in said intercalating composition is at least about 1% by weight.

4. A composition in accordance with claim 3, wherein the concentration of intercalant polymer in said intercalating composition is at least about 2% by weight.

5. A composition in accordance with claim 1, wherein the concentration of intercalant polymer in said intercalating composition is in the range of about 10%–60% by weight.

6. A composition in accordance with claim 4, wherein the concentration of intercalant polymer in said intercalating composition is at least about 15% by weight, based on the dry weight of layered material in the intercalating composition, to achieve spacing of said adjacent platelets of at least about 10 Å.

7. A composition in accordance with claim 6, wherein the concentration of intercalant polymer in said intercalating composition is at least about 20% by weight, based on the dry weight of layered material in the intercalating composition.

8. A composition in accordance with claim 7, wherein the concentration of intercalant polymer in said intercalating composition is at least about 30% by weight, based on the dry weight of layered material in the intercalating composition.

9. A composition in accordance with claim 1, wherein the concentration of intercalant polymer in said intercalating composition in the range of about 50% to about 90% by weight, based on the weight of polymer plus water.

10. A composition in accordance with claim 9, wherein the concentration of intercalant polymer in said intercalating composition is in the range of about 50% to about 80% by weight.

11. A composition in accordance with claim 1, wherein the concentration of intercalant polymer in the intercalating composition is at least about 16% by weight, based on the dry weight of the layered material.

12. A composition in accordance with claim 11, wherein the concentration of intercalant polymer in the intercalating composition is in the range of about 16% to about 70% by weight, based on the dry weight of the layered material.

13. A composition in accordance with claim 1, wherein the weight ratio of intercalant polymer to layered material in the intercalating composition is in the range of about 1:20 to about 10:1.

14. A composition in accordance with claim 11, wherein the weight ratio of intercalant polymer to layered material is at least 1:12.

15. A composition in accordance with claim 14, wherein the weight ratio of intercalant polymer to layered material in the intercalating composition is at least 1:5.

16. A composition in accordance with claim 15, wherein the weight ratio of intercalant polymer to layered material in the intercalating composition is in the range of 1:5 to 1:3.

17. A composition in accordance with claim 1, wherein the intercalant polymer is selected from the group consisting of polyvinylpyrrolidone; polyvinyl alcohol; polyvinylimine; and mixtures thereof.

18. A composition in accordance with claim 17, wherein the intercalant polymer is polyvinyl alcohol.

19. A composition in accordance with claim 13, wherein the intercalant polymer is polyvinylpyrrolidone.

20. A composition in accordance with claim 18, wherein the intercalant polymer is polyvinyl alcohol having less than about 5% by weight acetal substituents in the polymer.

21. A composition in accordance with claim 17, wherein the intercalant polymer has a weight average molecular weight in the range of about 100 to about 100,000.

22. A composition in accordance with claim 17, wherein the intercalant polymer has a weight average molecular weight in the range of about 200 to about 40,000.

23. A composition in accordance with claim 22, wherein the intercalant polymer is polyvinylpyrrolidone.

24. A composition in accordance with claim 22, wherein the intercalant polymer is a polyvinyl alcohol.

25. A composition in accordance with claim 1, wherein the intercalant polymer is a homopolymer or copolymer of N-vinylpyrrolidone.

26. A method of increasing the viscosity of an organic liquid by combining said organic liquid with about 0.05% to about 60% by weight of the composition of exfoliated platelets of an intercalate complex of a phyllosilicate having adjacent phyllosilicate platelets and an intercalant polymer comprising:

contacting the phyllosilicate, having a water content of at least about 4% by weight, with said intercalant polymer having a functionality selected from the group consisting of an aromatic ring; carbonyl; carboxyl; hydroxyl; amine; amide; ether; ester; an $SO_x$; a $PO_x$ structure and mixtures thereof, wherein x=2, 3, or 4, to form an intercalating composition having a weight ratio of intercalant polymer to phyllosilicate of at least 1:20, to form an intercalate, having about 8 grams of polymer per 100 grams of phyllosilicate to about 90 grams of polymer per 100 grams of phyllosilicate, without an onium ion or silane coupling agent, wherein intercalation of said polymer between said adjacent phyllosilicate platelets of said phyllosilicate is sufficient to space said adjacent phyllosilicate platelets a distance of at least about 5 Å;

exfoliating a predominance of said spaced phyllosilicate platelets; and combining said exfoliated platelets with said organic liquid.

27. The method of claim 26, wherein said intercalating composition includes a water intercalating carrier comprising about 4% to about 5000% by weight water, capable of dissolving said polymer, based on the dry weight of said phyllosilicate.

28. The method of claim 27, wherein said intercalating composition includes water in an amount of about 30% to about 40% by weight.

29. The method of claim 28, wherein said water content of said intercalating composition comprises about 35% to about 40% by weight, based on the dry weight of said phyllosilicate.

30. The method of claim 27, wherein said intercalating composition comprises about 5% to about 50% by weight water, based on the dry weight of said phyllosilicate.

31. The method of claim 27, wherein said intercalating composition includes water in an amount of about 7% to about 100% by weight, based on the dry weight of the phyllosilicate in the intercalating composition.

32. A composition comprising an organic liquid selected from the group consisting of monohydric alcohols, polyhydric alcohols and mixtures thereof, in an amount of about 40% to about 99.95% by weight of the composition and about 0.05% to about 60% by weight of the composition of exfoliated platelets of an intercalate of a phyllosilicate material having adjacent spaced platelet surfaces, said exfoliated platelets formed by contacting said phyllosilicate material, having a water content of at least about 4% by weight, with an intercalant polymer having a functionality selected from the group consisting of an aromatic ring; carbonyl; carboxyl; hydroxyl; amine; amide; ether; ester; an $SO_x$; a $PO_x$ structure and mixtures thereof, wherein x=2, 3, or 4, said polymer contacting said phyllosilicate material in an intercalating composition having a concentration of about 16% to about 90% polymer, based on the dry weight of said phyllosilicate material, to form said intercalate having said intercalant polymer sorbed between said adjacent spaced platelet surfaces of the phyllosilicate material and complexed on said platelet surfaces of said phyllosilicate material in a weight ratio of polymer to phyllosilicate material of 8 grams of polymer per 100 grams of phyllosilicate material to 90 grams of polymer per 100 grams of phyllosilicate material, without an onium ion or silane coupling agent, to expand the spacing between a predominance of the adjacent phyllosilicate platelet surfaces to at least about 5 Å, when measured after sorption of the polymer and drying of the intercalate to a maximum water content of 5% by weight, and exfoliating a predominance of said spaced phyllosilicate platelets.

33. The composition of claim 32, wherein the intercalate is exfoliated into a predominance of single platelets having said intercalant polymer complexed onto said platelet surfaces.

34. The composition of claim 32, wherein the alcohol is a monohydric alcohol having 1 to about 5 carbon atoms.

35. The composition of claim 32, wherein the alcohol is a polyhydric alcohol selected from the group consisting of glycols, glycerols, and mixtures thereof.

36. A composition in accordance with claim 32, wherein the intercalant composition has a weight ratio of intercalant polymer to phyllosilicate of at least about 1:20.

37. A composition in accordance with claim 36, wherein the weight ratio of intercalant polymer to phyllosilicate in said intercalating composition is at least about 1:12.

38. A composition in accordance with claim 37, wherein the weight ratio of intercalant polymer to phyllosilicate in said intercalating composition is at least about 1:10.

39. A composition in accordance with claim 38, wherein the weight ratio of intercalant polymer to phyllosilicate in said intercalating composition is at least about 1:5.

40. A composition in accordance with claim 39, wherein the weight ratio of intercalant polymer to phyllosilicate in said intercalating composition in the range of about 1:5 to about 9:1.

41. A composition in accordance with claim 40, wherein the weight ratio of intercalant polymer to phyllosilicate in said intercalating composition in the range of about 1:5 to about 1:3.

42. A composition in accordance with claim 36, wherein the concentration of intercalant polymer in the intercalating composition is at least about 16% by weight, based on the dry weight of the phyllosilicate.

43. A composition in accordance with claim 42, wherein the concentration of intercalant polymer in the intercalating composition is in the range of about 16% to about 70% by weight, based on the dry weight of the phyllosilicate.

44. A composition in accordance with claim 42, wherein the concentration of intercalant polymer in the intercalating composition is in the range of about 16% to less than about 35% by weight, based on the dry weight of the phyllosilicate.

45. A composition in accordance with claim 43, wherein the concentration of intercalant polymer in the intercalating composition is in the range of about 35% to less than about 55% by weight, based on the dry weight of the phyllosilicate.

46. A composition in accordance with claim 43, wherein the concentration of the intercalant polymer in the intercalating composition is in the range of about 55% to less than about 70% by weight, based on the dry weight of the phyllosilicate.

47. A composition in accordance with claim 32, wherein the organic liquid is selected from the group consisting of alcohols, ketones, aldehydes, esters, glycols, glycerols, or ethers and mixtures thereof.

48. A method of manufacturing a composition containing about 10% to about 99.95% by weight of an organic liquid and about 0.05% to about 60% by weight of exfoliated platelets of an intercalated layered material, said intercalated layered material having a water-soluble polymer intercalated between and bonded to adjacent platelet surfaces thereof through a bonding mechanism selected from the group consisting of ionic complexing; electrostatic complexing; chelation; hydrogen bonding; dipole/dipole; Van Der Walls forces; and any combination thereof, comprising:

contacting the layered material with a water-soluble intercalant polymer having a functionality selected from the group consisting of an aromatic ring; carbonyl; carboxyl; hydroxyl; amine; amide; ether; ester; an $SO_x$; a $PO_x$ structure and mixtures thereof, wherein x=2, 3, or 4 and water to form an intercalating composition, thereby forming an intercalate having said polymer intercalated between said adjacent platelets, without an onium ion or silane coupling agent, in an amount sufficient to space said adjacent platelets a distance of at least about 5 Å;

combining the intercalate with said organic liquid; and exfoliating the spaced platelets of said intercalate into predominantly individual platelets.

49. The method of claim 48, wherein said layered material is a phyllosilicate and said intercalating composition is an aqueous solution comprising about 4% to about 5000% by weight water, based on the dry weight of said phyllosilicate in said intercalating composition.

50. The method of claim 49, wherein said intercalating composition comprises about 30% to about 50% water, based on the dry weight of the phyllosilicate.

51. The method of claim 50, wherein said intercalating composition comprises about 35% to about 45% by weight water.

52. A method of manufacturing a composition comprising an organic liquid and exfoliated platelets of a phyllosilicate intercalate comprising:

contacting the phyllosilicate having adjacent spaced phyllosilicate platelets with a water-soluble intercalant polymer having a functionality selected from the group consisting of an aromatic ring; carbonyl; carboxyl; hydroxyl; amine; amide; ether; ester; an $SO_x$; a $PO_x$ structure and mixtures thereof, wherein x=2, 3, or 4 and water, wherein the weight ratio of the intercalant polymer to phyllosilicate is at least 1 to about 20, and the concentration of said water-soluble intercalant polymer is at least about 5% up to about 900% polymer, based on the dry weight of the phyllosilicate, to form said phyllosilicate intercalate having said intercalant polymer intercalated between said adjacent phyllosilicate platelets, without an onium ion or silane coupling agent, and in an amount sufficient to space said adjacent phyllosilicate platelets to a distance of at least about 5 Å;

combining the intercalate with said organic liquid; and exfoliating a predominance of the spaced phyllosilicate platelets.

53. A composition in accordance with claim 1, wherein the weight ratio of polymer to layered silicate material complexed between adjacent spaced layers of the layered silicate material is from about 16 grams of polymer per 100 grams of layered silicate material to about 90 grams of polymer per 100 grams of layered silicate material.

54. A composition in accordance with claim 53, wherein the layered silicate material is selected from the group consisting of montmorillonite; nontronite; beidellite; volksonite; hectorite; saponite; sauconite; sobockite; stevensite; svinfordite; vermiculite; illite; rectorite; tarosovite; ledikite; and mixtures thereof.

55. A composition in accordance with claim 53, wherein the weight ratio of polymer to layered silicate material complexed between adjacent spaced layers of the layered silicate material is from about 16 grams of polymer per 100 grams of layered silicate material to about 80 grams of polymer per 100 grams of layered silicate material.

56. A composition in accordance with claim 55, wherein the weight ratio of polymer to layered silicate material complexed between adjacent spaced layers of the layered silicate material is from about 20 grams of polymer per 100 grams of layered silicate material to about 60 grams of polymer per 100 grams of layered silicate material.

57. A composition in accordance with claim 14, wherein the weight ratio of intercalant polymer to layered silicate material in the intercalating composition is in the range of 1:20 to 1:3.

58. A composition in accordance with claim 6, wherein the concentration of intercalant polymer in said intercalating composition is about 15% to about 90% by weight, based on the dry weight of the layered silicate material in the intercalating composition.

59. A composition in accordance with claim 11, wherein the concentration of intercalant polymer in said intercalating composition is about 16% to about 90% by weight, based on the dry weight of the layered silicate material in the intercalating composition.

60. A composition in accordance with claim 59, wherein the concentration of intercalant polymer in said intercalating composition is about 16% to about 80% by weight, based on the dry weight of the layered silicate material in the intercalating composition.

61. A method in accordance with claim 26, wherein the weight ratio of polymer to phyllosilicate complexed between adjacent spaced layers of the phyllosilicate is from about 10 grams of polymer per 100 grams of phyllosilicate to about 90 grams of polymer per 100 grams of phyllosilicate.

62. A method in accordance with claim 61, wherein the weight ratio of polymer to phyllosilicate complexed between adjacent spaced layers of the phyllosilicate is from about 16 grams of polymer per 100 grams of phyllosilicate to about 90 grams of polymer per 100 grams of phyllosilicate.

63. A method in accordance with claim 62, wherein the weight ratio of polymer to phyllosilicate complexed between adjacent spaced layers of the phyllosilicate is from about 16 grams of polymer per 100 grams of phyllosilicate to about 80 grams of polymer per 100 grams of phyllosilicate.

64. A method in accordance with claim 63, wherein the weight ratio of polymer to phyllosilicate complexed between adjacent spaced layers of the phyllosilicate is from about 20 grams of polymer per 100 grams of phyllosilicate to about 60 grams of polymer per 100 grams of phyllosilicate.

65. A method in accordance with claim 26, wherein the weight ratio of intercalant polymer to phyllosilicate in the intercalating composition is in the range of 1:20 to 1:3.

66. A method in accordance with claim 26, wherein the concentration of intercalant polymer in said intercalating composition is about 15% to about 90% by weight, based on the dry weight of the phyllosilicate in the intercalating composition.

67. A method in accordance with claim 66, wherein the concentration of intercalant polymer in said intercalating composition is about 16% to about 90% by weight, based on the dry weight of the phyllosilicate in the intercalating composition.

68. A method in accordance with claim 67, wherein the concentration of intercalant polymer in said intercalating composition is about 16% to about 80% by weight, based on the dry weight of the phyllosilicate in the intercalating composition.

69. A composition in accordance with claim 32, wherein the weight ratio of polymer to phyllosilicate material complexed between adjacent spaced layers of the phyllosilicate material is from about 10 grams of polymer per 100 grams of phyllosilicate material to about 90 grams of polymer per 100 grams of phyllosilicate material.

70. A composition in accordance with claim 69, wherein the weight ratio of polymer to phyllosilicate material complexed between adjacent spaced layers of the phyllosilicate material is from about 16 grams of polymer per 100 grams of phyllosilicate material to about 90 grams of polymer per 100 grams of phyllosilicate material.

71. A composition in accordance with claim 70, wherein the weight ratio of polymer to phyllosilicate material complexed between adjacent spaced layers of the phyllosilicate material is from about 16 grams of polymer per 100 grams of phyllosilicate material to about 80 grams of polymer per 100 grams of phyllosilicate material.

72. A composition in accordance with claim 71, wherein the weight ratio of polymer to phyllosilicate material complexed between adjacent spaced layers of the phyllosilicate material is from about 20 grams of polymer per 100 grams of phyllosilicate material to about 60 grams of polymer per 100 grams of phyllosilicate material.

73. A composition in accordance with claim 36, wherein the weight ratio of intercalant polymer to phyllosilicate material in the intercalating composition is in the range of 1:20 to 1:3.

74. A composition in accordance with claim 32, wherein the concentration of intercalant polymer in said intercalating composition is about 16% to about 80% by weight, based on the dry weight of the phyllosilicate material in the intercalating composition.

75. A method in accordance with claim 48, wherein the weight ratio of polymer to layered material complexed between adjacent spaced layers of the layered silicate material is from about 8 grams of polymer per 100 grams of layered silicate material to about 90 grams of polymer per 100 grams of layered silicate material.

76. A method in accordance with claim 75, wherein the weight ratio of polymer to layered material complexed between adjacent spaced layers of the layered silicate material is from about 10 grams of polymer per 100 grams of layered silicate material to about 90 grams of polymer per 100 grams of layered silicate material.

77. A method in accordance with claim 76, wherein the weight ratio of polymer to layered material complexed between adjacent spaced layers of the layered silicate material is from about 16 grams of polymer per 100 grams of layered silicate material to about 80 grams of polymer per 100 grams of layered silicate material.

78. A method in accordance with claim 77, wherein the weight ratio of polymer to layered material complexed between adjacent spaced layers of the layered silicate material is from about 20 grams of polymer per 100 grams of layered silicate material to about 60 grams of polymer per 100 grams of layered silicate material.

79. A method in accordance with claim 48, wherein the weight ratio of intercalant polymer to layered material in the intercalating composition is in the range of 1:20 to 1:3.

80. A method in accordance with claim 48, wherein the concentration of intercalant polymer in said intercalating composition is about 15% to about 90% by weight, based on the dry weight of the layered material in the intercalating composition.

81. A method in accordance with claim 80, wherein the concentration of intercalant polymer in said intercalating composition is about 16% to about 90% by weight, based on the dry weight of the layered material in the intercalating composition.

82. A method in accordance with claim 81, wherein the concentration of intercalant polymer in said intercalating composition is about 16% to about 80% by weight, based on the dry weight of the layered material in the intercalating composition.

83. A method in accordance with claim 52, wherein the weight ratio of polymer to layered material complexed between adjacent spaced layers of the phyllosilicate is from about 8 grams of polymer per 100 grams of phyllosilicate to about 90 grams of polymer per 100 grams of phyllosilicate.

84. A method in accordance with claim 83, wherein the weight ratio of polymer to phyllosilicate complexed between adjacent spaced layers of the phyllosilicate is from about 16 grams of polymer per 100 grams of phyllosilicate to about 90 grams of polymer per 100 grams of phyllosilicate.

85. A method in accordance with claim 84, wherein the weight ratio of polymer to phyllosilicate complexed between adjacent spaced layers of the phyllosilicate is from about 16 grams of polymer per 100 grams of phyllosilicate to about 80 grams of polymer per 100 grams of phyllosilicate.

86. A method in accordance with claim 85, wherein the weight ratio of polymer to phyllosilicate complexed between adjacent spaced layers of the phyllosilicate is from about 20 grams of polymer per 100 grams of phyllosilicate to about 60 grams of polymer per 100 grams of phyllosilicate.

87. A method in accordance with claim 52, wherein the weight ratio of intercalant polymer to phyllosilicate in the intercalating composition is in the range of 1:20 to 1:3.

88. A method in accordance with claim 52, wherein the concentration of intercalant polymer in said intercalating composition is about 15% to about 90% by weight, based on the dry weight of the phyllosilicate in the intercalating composition.

89. A method in accordance with claim 88, wherein the concentration of intercalant polymer in said intercalating composition is about 16% to about 90% by weight, based on the dry weight of the phyllosilicate in the intercalating composition.

90. A method in accordance with claim 89, wherein the concentration of intercalant polymer in said intercalating composition is about 16% to about 80% by weight, based on the dry weight of the phyllosilicate in the intercalating composition.

* * * * *